United States Patent
Daga et al.

(10) Patent No.: US 12,154,447 B2
(45) Date of Patent: Nov. 26, 2024

(54) SYSTEM AND METHOD TO ANALYZE AND IMPROVE SPORTS PERFORMANCE USING MONITORING DEVICES

(71) Applicant: STR8BAT SPORTS TECH SOLUTIONS PTE. LTD.

(72) Inventors: Gagan Daga, Bangalore (IN); Rahul Nagar, Bangalore (IN); Reetesh Kapahi, Bangalore (IN)

(73) Assignee: STR8BAT SPORTS TECH SOLUTIONS OTE, Singapore (SG)

( * ) Notice: Subject to any disclaimer, the term of this patent is extended or adjusted under 35 U.S.C. 154(b) by 1241 days.

(21) Appl. No.: 16/335,194

(22) PCT Filed: Sep. 4, 2017

(86) PCT No.: PCT/IN2017/050398
§ 371 (c)(1),
(2) Date: Mar. 20, 2019

(87) PCT Pub. No.: WO2018/055635
PCT Pub. Date: Mar. 29, 2018

(65) Prior Publication Data
US 2019/0347956 A1  Nov. 14, 2019

(30) Foreign Application Priority Data

Sep. 22, 2016 (IN) .............................. 201641032413

(51) Int. Cl.
| | | |
|---|---|---|
| G09B 19/00 | (2006.01) | |
| G06N 20/00 | (2019.01) | |
| G09B 9/00 | (2006.01) | |

(52) U.S. Cl.
CPC ......... G09B 19/0038 (2013.01); G06N 20/00 (2019.01); G09B 9/00 (2013.01)

(58) Field of Classification Search
None
See application file for complete search history.

Primary Examiner — James B Hull
(74) Attorney, Agent, or Firm — Joy S Goudie

(57) ABSTRACT

The embodiments herein provide a method and system for monitoring, analyzing, improving and giving instant feedback on sports performance of an individual. The embodiments also provide a system and method to create visual representation of a sports action without the use of any visual data capture mechanisms. The system includes a game monitoring device, a communication network, a remote server, and a computing device. The remote server comprises a filtering and signal processing module, an analytics module, a database, and an artificial intelligence module. The computing device incudes several modules and a user interface. The game monitoring device detects several data points from the player and transmits the same to the remote server. The remote server filters and processes the signals for analyzing each shot and the game of the player. The analysis is visualized and displayed on the user computing device.

24 Claims, 32 Drawing Sheets

SYSTEM AND METHOD TO ANALYZE AND IMPROVE SPORTS PERFORMANCE USING MONITORING DEVICES

CROSS-REFERENCE TO RELATED APPLICATIONS

This application is a national phase application of the Patent Cooperation Treaty (PCT) international application with serial number PCT/IN2017/050398 filed in the Indian Patent Office on Sep. 14,2017 with the title "A SYSTEM AND METHOD TO ANALYZE AND IMPROVE SPORTS PERFORMANCE USING MONITORING DEVICES", and claims the priority and the benefit of the Provisional Patent Application with serial number 201641032413, filed in the Indian Patent Office on Sep. 22, 2016, with the title "A SYSTEM AND METHOD TO ANALYZE AND IMPROVE SPORTS PERFORMANCE USING MONITORING DEVICES". The contents of berth the Provisional Patent Application and the PCT international application are incorporated in their entirety by reference herein.

BACKGROUND

Technical field

The embodiments herein are generally related to monitoring systems. The embodiments herein are particularly related to sports monitoring systems. The embodiments herein are more particularly related to a system and method for monitoring, analysis and providing an instant feedback to a player on his performance action while playing a sport.

Description of the Related Art

The limits of human performance in sports are pushed in keeping with the Olympic motto output: "Faster, Higher, Stronger". This has kept the players, sports scientists, coaches and sport technology innovators for continuously looking for ways to improve the performance of the players. The development of technology and better computing systems has also attracted the attention of people attention towards monitoring and analyzing each movement played in a game of sport. The demand for monitoring and analysis has grown even more significantly with the increased usage of digital media.

The performance of a player and a team is monitored and analyzed through a methodical training process to help the player and team to improve techniques and team performances through a continuous feedback process. The performance analysis also helps the players and coaches to identify good and bad performances of a player and facilitate comparative analysis of teams and players. Performance analysis also helps the players and coaches to rank performances against a baseline and leader-board.

The conventional state-of-art systems use a wide variety of equipments and methods for monitoring and analyzing the performance of an individual player and the team. However, the conventional systems are resource intensive and use a plurality of paraphernalia for monitoring and analysis. Further, these conventional systems are used for highly professional players for highly competitive tournaments.

Therefore, there is a need for a ubiquitous system and method for monitoring and analyzing a game of a player in (near) real-time. Further, there is a need for a system and method for providing a deep analysis of the techniques and performance of the player and team for improving their game and skill. Still farther, there is a need for a system and method for providing an instant feedback on the performance of a player during a game in progress. Still further, there is a need for a system and method for providing an in-person or remote coaching for the player and the playing team during a game.

The above-mentioned shortcomings, disadvantages and problems are addressed herein and which will be understood by reading and studying the following specification.

OBJECT OF THE EMBODIMENTS HEREIN

The primary object of the embodiments herein is to provide a system and method for monitoring a game involving bat and ball through a plurality of monitoring devices, and a plurality of sensors.

Another object of the embodiments herein is to provide a game or sports monitoring device with a plurality of sensors for receiving or collecting a plurality of data points and transmitting the same to a remote server.

Yet another object of the embodiments herein is to provide a system and method for analyzing the received data points and deriving an actionable insight.

Yet another object of the embodiments herein is to provide a system and method to present the derived actionable insight to on a computing device.

Yet another object of the embodiment herein is to provide a system and method to generate a visual simulation of the actions captured by the device without using any video recording equipment or an image capturing device.

Yet another object of the embodiments herein is to provide a system and method to generate a common platform for the coaches ant players to share actionable insights and create a ranking.

These and other objects and advantages of the embodiments herein will become readily apparent from the following summary and the detailed description taken in conjunction with the accompanying drawings.

SUMMARY

The following details present a simplified summary of the embodiments herein to provide a basic understanding of the several aspects of the embodiments herein. This summary is not an extensive overview of the embodiments herein. It is not intended to identify key/critical elements of the embodiments herein or to delineate the scope of the embodiments herein. Its sole purpose is to present the concepts of the embodiments herein in a simplified form as a prelude to the more detailed description that is presented later.

The other objects and advantages of the embodiments herein will become readily apparent from the following description taken in conjunction with the accompanying drawings.

The various embodiments herein provide a system and method for monitoring and analyzing a game which includes a ball and a bat or a racket. According to an embodiment herein, a system for monitoring and analyzing a cricket game is provided. The system comprises a game monitoring device/s, a communication network, a remote server, and a computing device. The remote server comprises a plurality of modules including, but not limited to a filtering and signal processing module, an analytics module, a database, and an artificial intelligence module. The computing device includes a plurality of modules along with a user interface.

According to one embodiment herein, the game monitoring device comprises a plurality of sensors for detecting a plurality of data points or parameters from the player and sports equipment or accessories used or worn by the player. The plurality of detected data points or parameters is transmitted to a paired computing device which in turn is the gateway to the remote server. The paired computing device is configured to filter and processes the signals for analyzing each shot, action, pose, movement and game of the player during a game/sport in action. The analysis is visualized and displayed on the computing device of a user. The game monitoring device/s, computing device/the gateway device and the remote server are configured to communicate with each other through a communication network.

According to an embodiment herein, a system is provided for analyzing sports and improving performance by providing feedbacks in near real time without any visual data capture mechanisms. The system comprises a monitoring device, and wherein the monitoring device comprises a plurality of sensors for detecting a plurality of data points from a plurality of actions and poses comprised in a physical motion of a player. The game monitoring device/s includes a plurality of sensors that capture a plurality of parameters of the player and game devices. The parameters captured by the sensors of the game devices include but not limited to a motion of the player, a speed at which the player has hit the ball, an angular motion, a direction of the shot, an impact force, an amount of pressure put on the ball by the bat, a type of shot, pitch direction, a plurality of physiological features of the player, and the like. The plurality of sensors includes motion sensors, pressure sensors, position sensors, proximity sensors, speed sensors, an audio sensor, a pyroelectric sensor, and a piezoelectric sensor. The plurality of sensors preferably comprises a gyro sensor, accelerometer, magnetometer or compass, etc.

According to an embodiment herein, a remote server is provided to communicatively connect with the monitoring device. The remote server comprises a filtering and signal processing module, a database module, an analytics module and an artificial intelligence module. The filtering and signal processing module is connected to the monitoring device and configured to filter unwanted noise signals received from the plurality of sensors in the monitoring device. The analytics module is connected to the filtering and signal processing module and configured to analyze the output signals from the filtering and signal processing module based on preset rules and pre-determined techniques to compare an action and performance of the player with a reference template of best or practices or ways of performing the physical motion, action or pose to provide a feedback to the player for improving a performance of the player.

A database is connected to the remote server and configured to store the analysis data for future reference and retrieval data, meta-data, information related to a plurality of physical motion of a plurality of players. The artificial intelligence module is configured to process the stored data to provide a predictive analytics on the physical motion, action or pose of the player. A plurality of end-point computing devices is connected to the remote server.

According to an embodiment herein, the monitoring device, the plurality of sensors, the remote server, the filtering and signal processing module, the database module, the analytics module and the artificial intelligence module are communicatively connected with each other through a wireless communication network.

According to an embodiment herein, a user computing device is loaded with a software for processing the data or parameters collected with the plurality of sensors to provide a simulation of play to the user and a feedback on the game played.

According to one embodiment herein, the monitoring device comprises a plurality of inertial measurement sensor modules and magnetometer module. The inertial measurement sensors module comprises accelerometer and gyroscope modules. The motion data from the inertial measurement sensor module is transmitted to the gaming engine. The gaming engine is configured to enable a post-noise filtering and error correction in the measured data. The motion is recreated in 3D visual space using a plurality of data points measured using the inertial measurement sensors.

According to one embodiment herein, a microphone is also provided to distinguish an actual action played with the bat and an unwanted movement or action of bat and player.

According to one embodiment herein, the monitoring device is configured to measure a plurality of parameters and common data points including but not limited to quaternions, linear acceleration in three axes, angular velocity and rotational parameters including roll, pitch and yaw values.

According to one embodiment herein, the monitoring device is placed in a plurality of locations on the sports gear and sports attire of a player. The number of monitoring devices and the configuration of the monitoring devices are determined or estimated by a plurality of parameters. The plurality of parameters induce a location and placement of the monitoring device on sports equipment, an impact threshold value, visual context, background and scorecard list. The location and placement of the monitoring device on the sports equipment, accessory and sportswear is determined based on an axis orientation, three-axis of the device and speed of motion of the sports equipment. The impact threshold parameter is configured to capture the point of impact based on the type of sport and sport activity. The parameters for determination of impact include acceleration and a rate of change of acceleration. The parameters for visual context, background and scorecard list are configured specifically to a particular kind of sport activity.

According to an embodiment herein, the computing device is configured to receive an output data from the plurality of sensors to generate a visual simulation of the actions captured by the monitoring device without using any video recording equipment. The computing device is configured to generate a common platform for a plurality of coaches and players to share actionable insights and create a ranking of each player. The computing device is configured to provide a simulation of the physical motion captured through the monitoring device in a plurality of computing devices.

According to an embodiment herein, the paired user computing device is configured to receive an output data from the plurality of sensors to generate a visual simulation of the actions captured by the monitoring device without using any video recording equipment.

According to an embodiment herein, the monitoring device comprises a communication circuit for storing and transmitting the monitored data points to a remote computing device, or the remote server. The plurality of sensors in the monitoring device is placed in the vicinity of the player or mounted or embedded in an attire or a plurality of equipments used by the player in performing a plurality of physical actions or poses. The monitoring device is configured to filter noise signals or unwanted spurious signals from the output data received from the plurality of sensors. The monitoring device is configured to detect data points and processes the output signals from the plurality of sensors to derive a pattern. The monitoring device is configured to synchronize the plurality of sensors, so that the plurality of data points received from the plurality of sensors is used to generate a visual simulation of the players for providing a feedback in near real time.

According to an embodiment herein, the analytics module is configured to analyze the information and the output data from the monitoring device. The analytics module is configured to contextually render the output data from the monitoring device in a plurality of end-point computing devices based on preset rules. The end-point devices are configured to access the remote server to access any data stored in the remote server for reference and retrieval in future.

According to an embodiment herein, the analytics module is configured to analyze the output data from the monitoring device in a plurality of end-point computing devices based on preset parameters. The preset parameters for analysis includes a position of the bat, a direction of the shot, a type of the shot, a swing analysis, a shot analysis, a direction analysis, a pressure analysis, a pattern determination and a comparative analysis, a virtual replay of the game, and a mechanics of the game.

According to an embodiment herein, the analytics module is configured to provide a comparison of an action of player in a game with the best practice/template/reference shot. The analytics module is configured to provide a guidance on necessary changes or improvements needed to reach to the level of standard/template shots. The guidance and analysis information is provided in a plurality of segments with a color coding for enhanced analysis.

According to an embodiment herein, the analytics module is configured to combine analysis of each shot to derive analysis report for each delivery, game, session, player, and wherein the analysis module is configured to combine a plurality of game patterns of the player to derive optimum factors or parameters for the player, and wherein optimum factors or parameters for the player includes a body dynamics of the player relative to the bat position at the time of impact for increasing a game performance, and unfavorable environmental factors to the player.

According to an embodiment herein, the monitoring device, the remote server, and the plurality of computing devices are connected through a communication network for establishing a wired and wireless communication. The communication network includes, but not limited to the internet, an intranet, a radio-frequency network, telephonic network, a local area network (LAN), a wide area network (WAN), a proximity network such as Bluetooth, NFC, Wi-Fi, ZigBee, and Bluetooth Low Energy (BLE).

According to an embodiment herein, the mobile device is configured to enable a plurality of computing devices, to interface with the remote server. The mobile device is configured to communicate with the remote server and the plurality of computing devices through a plurality of communication protocols.

According to an embodiment herein, the plurality of sensors in the monitoring device is communicatively connected through wireless network to synchronize a capturing of information or data or an event of a physical motion. The plurality of sensors is configured to capture an information simultaneously. The plurality of sensors is configured to recreate an event from the synchronously captured information even when one of the sensors has failed to capture an event.

According to an embodiment herein, the artificial intelligence (AI) module is configured to automatically identify noise from detected and received information from the plurality of sensors and monitoring device. The AI module is configured to contextually determine and identify noise from useful information. The AI module processes the digital data, applies stochastic filters to determine if the ball impact is actually a legitimate shot or any other motion like gardening of pitch, high speed rotation of bat, dragging of the bat. The AI module is configured to generate an automated audio and text commentary of the physical motion, actions or poses that are captured using the system.

According to an embodiment herein, the artificial intelligence module is configured to learn from the stored previous data or past data of historical data of the player to provide predictive analytics at a plurality of levels. The plurality of levels includes a player level analytics, a game level analytics and a session-level analytics, and wherein the artificial intelligence module is configured to predict the common mistakes or errors made by the player based on the analysis of past or previous games to provide a recommendation to help the player to overcome or avoid the errors in the game on action, and wherein the artificial intelligence module is configured to provide recommendations to enhance skill and performance of the player. The embodiment comprises a machine learning module, which is configured to identify patterns from the observed data and provide contextual suggestions on the user's computing device.

According to an embodiment herein, the plurality of end-point devices is configured to communicate with the remote server. The plurality of end-point devices is configured to analyze the stored past data of physical actions, poses or motion of a user and quantitatively analyze the physical actions, by comparing the preset or observed data from the same user or a plurality of other users or with a reference data stored and archived in the database.

According to an embodiment herein, the system further comprises a user interface for displaying analysis, visuals and results computed by the remote server. The user interface is configured to display a plurality of information of the player and the game. The plurality of information displayed on the user computing device through the user interface include a visual playback of the previous shots played by the player, analysis and visualization of the previous shots played by the player, analysis and visualization of the previous games played by the player, comparative analysis of the game and shots of the player with a plurality of other players.

According to an embodiment herein, the remote server is configured to provide connectivity with a plurality of computing devices for establishing inter-channel communication, and wherein the plurality of computing devices include a computing device of a player, a computing device of a coach and a computing device of a physician, and wherein the computing device of the player is connected to the computing devices of the coach and the computing device of the physician to enable the player to receive personal counseling from the physician and coach based on a complete analysis of the player and a game data of the player, and wherein the remote server is configured to enable the users/players for sharing the analyzed data and results to third-party networks, and wherein the third party networks is a social networking sites.

According to an embodiment herein, the monitoring device further comprises an impact sensor module. The impact sensor module is configured to detect and determine an impact of a ball on a bat. The impact sensor module is configured to determine a position of a plurality of sensors that is attached to the bat, the ball and a human user.

According to an embodiment herein, the plurality of end-point devices are configured to simulate a virtual rendering of a real-world human action, based on the output of the impact sensor module and the plurality of sensors in the monitoring device. The plurality of end-point devices is configured to enable an integrated rendering of the simulated virtual rendering and real-world human actions.

According to an embodiment herein, a microphone module is provided on the bat used by a player. The microphone module is connected to the communication module. The microphone module is configured to transmit an audio information related to the impact of bat with other player accessories and to help triangulate exact impact time during the bat swing.

According to an embodiment herein, the noise and filtering module is configured to automatically identify noise from information. The noise and filtering module is further configured to contextually determine and identify noise from useful information and pattern.

According to an embodiment herein, a bat is a ball hitting device used by the player engaged in a sports activity, and wherein the bat is a cricket bat, or a tennis racquet or a badminton racquet or a baseball bat, or a table tennis bat or a hockey stick.

According to an embodiment herein, the ball is a cricket ball or tennis ball or badminton shuttle cock, or baseball, or table tennis ball or hockey ball.

According to an embodiment herein, the sports activity/event is cricket or hockey or baseball or tennis or table tennis.

According to an embodiment herein, a method is provided for analyzing sports and improving performance by providing feedbacks in near real time without any visual data capture mechanisms. The method comprises: collecting a plurality of data points with a plurality of sensors provided in a monitoring device; pairing a plurality of computing devices with the monitoring device for processing the collected data points and a plurality of signals; synchronizing the data collected from the plurality of sensors to recreate or simulate an action of the player in near real time, processing the collected data points with the computing device to provide a visual feedback on the actions or pose; generating and rendering a visual simulation of the actions captured by the monitoring device on a plurality of end-point computing devices, without using any video recording equipment; and contextual rendering of the processed data in the plurality of end-point computing devices. The monitoring device is configured to detect a plurality of data points from a plurality of actions and poses comprised in a physical motion of a player. The plurality of data points or parameters captured by the plurality of sensors include a motion of the player, a speed at which the player hits the ball, an angular motion, a direction of the shot, an amount of pressure put on the ball by the bat, and a plurality of physiological features of the player. One of the pluralities of sensors acts as a point of reference for synchronizing the data from a plurality of sensors. The computing device comprises a filtering and signal processing module, a database module, an analytics module, a machine learning module and an artificial intelligence module. The analytics module is configured to analyze the output signals from the filtering and signal processing module based on preset rules and predetermined techniques to compare an action and performance of the player with a reference template of best or practices or ways of performing the physical motion, action or pose to provide a feedback to the player for improving a performance of the player. The database is configured to store the analysis data for future reference and retrieval data, meta-data, information related to a plurality of physical motion of a plurality of players. The artificial intelligence module is configured to process the stored data to provide a predictive analytics on the physical motion, action or pose of the player.

According to an embodiment herein, a method is provided for analyzing sports and improving performance further comprises: transmitting the monitored data points to a remote computing device through a communication circuit configured in the monitoring device; detecting data points and processes the output signals to derive a pattern with the monitoring device; and synchronizing the plurality of sensors to fuse the plurality of data points received from the plurality of sensors to generate a visual simulation of the player and actions of the player in near real time. The method further comprises performing a post-noise filtering and error correction in the measured data with a gaming engine module.

According to an embodiment herein, the plurality of data points from a plurality of actions and poses of a player is detected with the monitoring device. The monitoring device comprises a gyroscope, an accelerometer, and a magneto meter or a compass, motion sensors, temperature sensors, pressure sensors, position sensors, proximity sensors, speed sensors, an audio sensor, a pyroelectric sensor, and a piezoelectric sensor, a communication module, a microcontroller, a memory, and a battery power supply.

According to an embodiment herein, an analysis of output data from the monitoring device is performed on the analytics module. The output data from the monitoring device is contextually rendered in a plurality of end-point computing devices by the analytics module based on preset rules. The end-point devices are configured to access the remote server to access any data stored in the remote server.

According to an embodiment herein, an analysis of output data from the monitoring device is performed on the analytics module. The analytics module is configured to run on a plurality of end-point computing devices based on preset parameters. The preset parameters for analysis includes a position of the bat, a direction of the shot, a type of the shot, a swing analysis, a shot analysis, a direction analysis, a pressure analysis, an audio analysis, a pattern determination, and a comparative analysis, a virtual replay of the game, and a mechanics of the game.

According to an embodiment herein, the analytics module is configured to combine analysis of each shot to derive analysis report far each delivery, game, session and player. The analysis module is configured to combine a plurality of game patterns of the player to derive optimum factors or parameters for the player. Optimum factors or parameters for the player include a body dynamics of the player relative to the bat position at the time of impact for increasing a game performance.

According to an embodiment herein, the plurality of sensors in the monitoring device is communicatively connected through wireless network to synchronize a capturing of information or data or an event or a physical motion. The plurality of sensors is configured to capture an information of an event simultaneously. The plurality of sensors is configured to recreate an event from the synchronously captured information even when one of the sensors has failed to capture an event.

According to an embodiment herein, the artificial intelligence module is configured to automatically identify noise from information. The artificial intelligence module is configured to contextually determine and identify noise from useful information.

According to an embodiment herein, the noise and filtering module is configured to automatically identify noise from information. The noise and filtering module is configured to contextually determine and identify noise from useful information and pattern.

According to an embodiment herein, the artificial intelligence module is configured to generate an automated audio and text commentary of the physical motion, actions or poses that are captured.

According to an embodiment herein, the artificial intelligence module is configured to learn from the stored previous data or historical data of the player to provide predictive analytics at a plurality of levels. The plurality of levels includes a player level analytics, a game level analytics, and a match level analytics. The artificial intelligence module is configured to predict common mistakes or errors made by the player based on the analysis of past or previous games to provide a recommendation to help the player to overcome or avoid the errors in the game on action, and wherein the artificial intelligence module is configured to provide recommendations to enhance skill and performance of the player.

According to an embodiment herein, wherein the plurality of end-point devices is configured to communicate with the remote server. The plurality of end-point devices is configured to analyze the stored past data of physical actions, poses or motion of a user and quantitatively analyze the physical actions, by comparing the preset or observed data from the same user/player or a plurality of other users/players.

According to an embodiment herein, the method further comprises displaying analysis, visuals and results computed by the remote server through a user interface. The user interface is configured to display a plurality of information of the player and the game. The plurality of information displayed on the user computing device through the user interlace include a visual playback of the previous shots played by the player, analysis and visualization of the previous shots played by the player, analysis and visualization of the previous games played by the player, comparative analysis of the game and shots of the player with a plurality of other players.

According to an embodiment herein, the monitoring device comprises an impact sensor module. The impact sensor module is configured to detect and determine an impact of a ball on a bat, and wherein the impact sensor module is configured to determine a position of a plurality of sensors that is attached to the bat, the ball and a player. The sensor on the bat of the player is the hub for all the sensors. An impact of the bail on the bat is used to trigger or activate all sensors to start recording the actions. The time of impact is the reference point for starting a recording operation According to an embodiment herein, a microphone module is provided on the bat used by a player. The microphone module is connected to the communication module. The microphone module transmits audio information related to the impact of bat with other player accessories.

The embodiments herein provide a system and method for monitoring and analyzing a game involving a ball and a bat. The examples of the ball and bat game include, but are not limited to cricket, golf, tennis, badminton, baseball. A game monitoring device/s is/are placed or in the vicinity of a player or attached to the game devices of the player or attached to the sports gear on the player, for receiving a plurality of the data points from the user. The game monitoring device/s includes a plurality of sensors that capture a plurality of parameters of the player and game devices. The parameters captured by the sensors of the game devices include, but are not limited to motion of the player, speed at which the player has hit the ball, angular motion and direction of the shot, best in class ball bowled, ball release point and angle, a plurality of physiological features of the player, and the like.

These and other aspects of the embodiments herein will be better appreciated and understood when considered in conjunction with the following description and the accompanying drawings, it should be understood, however, that the following descriptions, while indicating preferred embodiments and numerous specific details thereof, are given by* way of illustration and not of limitation. Many changes and modifications may be made within the scope of the embodiments herein without departing from the spirit thereof, and the embodiments herein include all such modifications.

BRIEF DESCRIPTION OF THE DRAWINGS

The other objects, features and advantages will occur to those skilled in the art from the following description of the preferred embodiment and the accompanying drawings in which.

Figure 1:
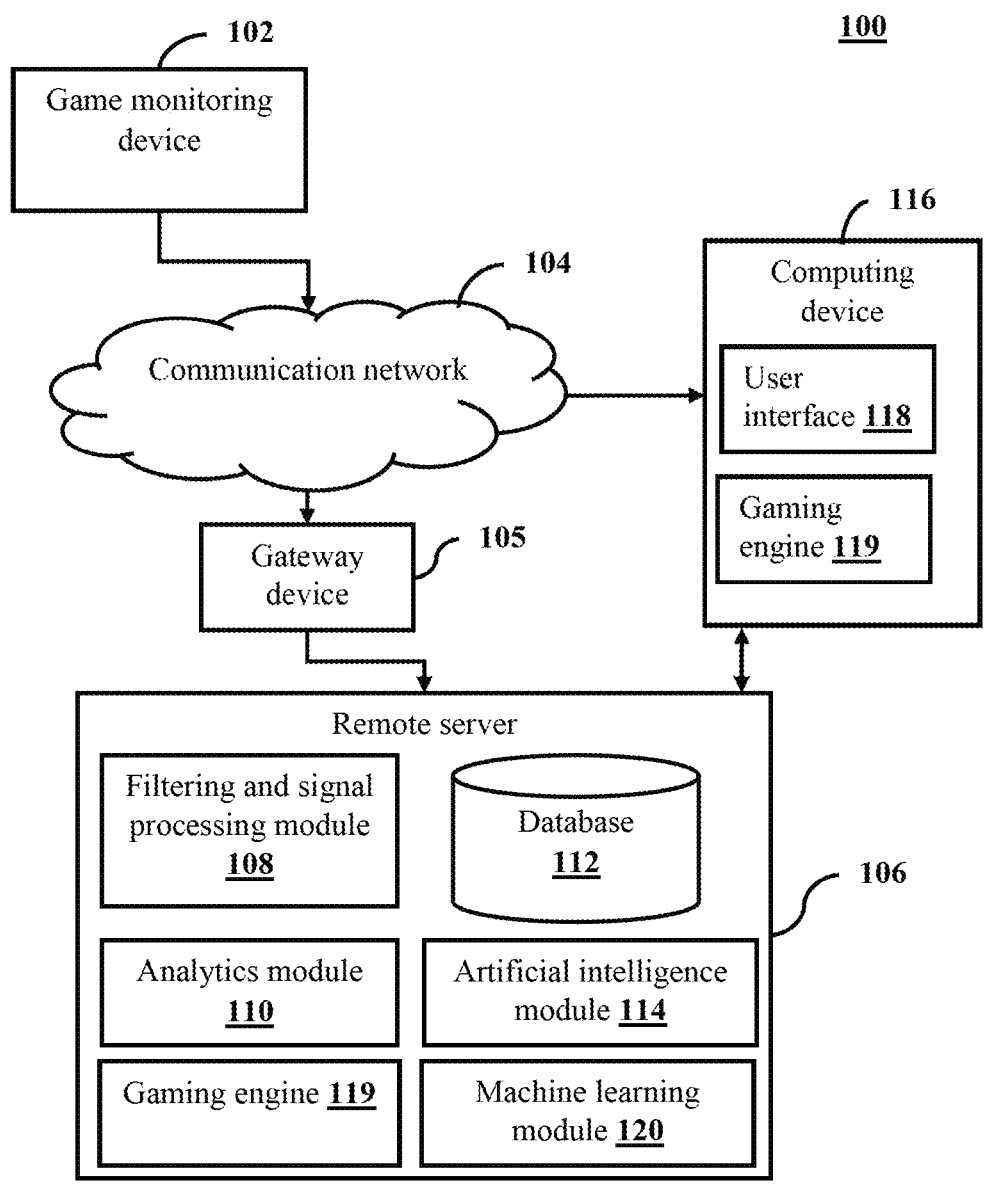
FIG. 1 illustrates a block diagram of a system for monitoring and analyzing sports performance of a player, according to one embodiment herein.

Although the specific features of the embodiments herein are shown in some drawings and not in others. This is done for convenience only as each feature may be combined with any or all of the other features in accordance with the embodiment herein.

DETAILED DESCRIPTION OF THE EMBODIMENTS HEREIN

In the following detailed description, a reference is made to the accompanying drawings that form a part hereof, and in which the specific embodiments that may be practiced is shown by way of illustration. These embodiments are described in sufficient detail to enable those skilled in the art to practice the embodiments and it is to be understood that the logical, mechanical and other changes may be made without departing from the scope of the embodiments. The following detailed description is therefore not to be taken in a limiting sense.

The various embodiments herein provide a system and method for monitoring and analyzing a game which includes a ball and a bat or a racket. According to an embodiment herein, a system for monitoring and analyzing a cricket game is provided. The system comprises a game monitoring device/s, a communication network, a remote server, and a computing device. The remote server comprises a plurality of modules including, but not limited to a filtering and signal processing module, an analytics module, a database, and an artificial intelligence module. The computing device includes a plurality of modules along with a user interface. The embodiment comprises a machine learning module, which is configured to identify patterns from the observed data to provide contextual suggestions on the user's computing device.

According to one embodiment herein, the game monitoring device comprises a plurality of sensors for detecting a plurality of data points or parameters from the player and sports equipment or accessories used or worn by the player. The plurality of detected data points or parameters are transmitted to a paired computing device and to the remote server. The remote server is configured to filter and processes the signals for analyzing each shot, action, pose, movement and game of the player during a game/sport in action. The analysis is visualized and displayed on the computing device of a user. The game monitoring device/s, the gateway device, the remote server, and the computing device are configured to communicate with each other through a communication network.

According to an embodiment herein, a system is provided for analyzing sports and improving performance by providing feedbacks in near real time without any visual data capture mechanisms. The system comprises a monitoring device, and wherein the monitoring device comprises a plurality of sensors for detecting a plurality of data points from a plurality of actions and poses comprised in a physical motion of a player. The game monitoring device/s includes a plurality of sensors that capture a plurality of parameters of the player and game devices. The parameters captured by the sensors of the game devices include but not limited to a motion of the player, a speed at which the player has hit the ball, an angular motion, a direction of the shot, an impact force, an amount of pressure put on the ball by the bat, a type of shot, pitch direction, a plurality of physiological features of the player, and the like. The plurality of sensors includes motion sensors, pressure sensors, position sensors, proximity sensors, speed sensors, an audio sensor, a pyroelectric sensor, and a piezoelectric sensor. The plurality of sensors preferably comprises a gyro sensor, accelerometer, magnetometer or compass, etc.

According to an embodiment herein, a remote server is provided to communicatively connect with the monitoring device. The remote server comprises a filtering and signal processing module, a database module, an analytics module and an artificial intelligence module. The filtering and signal processing module is connected to the monitoring device and configured to filter unwanted noise signals received from the plurality of sensors in the monitoring device. The analytics module is connected to the filtering and signal processing module and configured to analyze the output signals from the filtering and signal processing module based on preset rules and pre-determined techniques to compare an action and performance of the player with a reference template of best or practices or ways of performing the physical motion, action or pose to provide a feedback to the player for improving a performance of the player.

A database is connected to the remote server and configured to store the analysts data for future reference and retrieval data, meta-data, information related to a plurality of physical motion of a plurality of players. The artificial intelligence module is configured to process the stored data to provide a predictive analytics on the physical motion, action or pose of the player. A plurality of end-point computing devices is connected to the remote server.

According to an embodiment herein, the monitoring device, the plurality of sensors, the remote server, the filtering and signal processing module, the database module, the analytics module and the artificial intelligence module are communicatively connected with each other through a wireless communication network. A gateway device is communicatively connected to the monitoring device and the remote server.

According to an embodiment herein, a user computing device is loaded with a software for processing the data or parameters collected with the plurality of sensors to provide a simulation of play to the user and a feedback on the game played.

According to one embodiment herein, the monitoring device comprises a plurality of inertial measurement sensor modules and magnetometer module. The inertial measurement sensors module comprises accelerometer and gyroscope modules. The motion data from the inertial measurement sensor module is transmitted to the gaming engine. The gaming engine is configured to enable a post-noise filtering and error correction in the measured data. The motion is recreated in 3D visual space using a plurality of data points measured using the inertial measurement sensors.

According to one embodiment herein, a microphone is also provided to distinguish an actual action played with the bat and an unwanted movement or action of bat and player.

According to one embodiment herein, the monitoring device is configured to measure a plurality of parameters and common data points including but not limited to quaternions, linear acceleration in three axes, angular velocity and rotational parameters including roll, pitch and yaw values.

According to one embodiment herein, the monitoring device is placed in a plurality of locations on the sports gear and sports attire of a player. The number of monitoring devices and the configuration of the monitoring devices are determined or estimated by a plurality of parameters. The plurality of parameters includes a location and placement of the monitoring device on sports equipment, an impact threshold value, visual context, background and scorecard list. The location and placement of the monitoring device on the sports equipment, accessory and sportswear is determined based on an axis orientation, three-axis of the device and speed of motion of the sports equipment. The impact threshold parameter is configured to capture the point of impact based on the type of sport and sport activity. The parameters for determination of impact include acceleration and a rate of change of acceleration. The parameters for visual context, background and scorecard list are configured specifically to a particular kind of sport activity.

According to an embodiment herein, the remote server is configured to receive an output data from the plurality of sensors to generate a visual simulation of the actions captured by the monitoring device without using any video recording equipment. The remote server is configured to generate a common platform for a plurality of coaches and players to share actionable insights and create a ranking of each player. The remote server is configured to provide a simulation of the physical motion captured through the monitoring device in a plurality of computing devices.

According to an embodiment herein, the paired user computing device is configured to receive on output data from the plurality of sensors to generate a visual simulation of the actions captured by the monitoring device without using any video recording equipment.

According to an embodiment herein, the monitoring device comprises a communication circuit for storing and transmitting the monitored data points to a remote computing device, or the remote server. The plurality of sensors in the monitoring device is placed in the vicinity of the player or mounted or embedded in an attire or a plurality of equipments used by the player in performing a plurality of physical actions or poses. The monitoring device is configured to filter noise signals or unwanted spurious signals from the output data received from the plurality of sensors. The monitoring device is configured to detect data points and processes the output signals from the plurality of sensors to derive a pattern. The monitoring device is configured to synchronize the plurality of sensors, so that the plurality of data points received from the plurality of sensors is used to generate a visual simulation of the players for providing a feedback in near real time.

According to an embodiment herein, the analytics module is configured to analyze the information and the output data from the monitoring device. The analytics module is configured to contextually render the output data from the monitoring device in a plurality of end-point computing devices based on preset rules. The end-point devices are configured to access the remote server to access any data stored in the remote server for reference and retrieval in future.

According to an embodiment herein, the analytics module is configured to analyze the output data from the monitoring device in a plurality of end-point computing devices based on preset parameters. The preset parameters for analysis include a position of the bat, a direction of the shot, a type of the shot, a swing analysis, a shot analysis, a direction analysis, a pressure analysis, a pattern determination and a comparative analysis, a virtual replay of the game, and a mechanics of the game.

According to an embodiment herein, the analytics module is configured to provide a comparison of an action of player in a game with the best practice/template/reference shot. The analytics module is configured to provide a guidance on necessary changes or improvements needed to reach to the level of standard/template shots. The guidance and analysis information is provided in a plurality of segments with a color coding for enhanced analysis.

According to an embodiment herein, the analytics module is configured to combine analysis of each shot to derive analysis report for each delivery, game, session, player, and wherein the analysis module is configured to combine a plurality of game patterns of the player to derive optimum factors or parameters for the player, and wherein optimum factors or parameters for the player includes a body dynamics of the player relative to the bat position at the time of impact for increasing a game performance, and unfavorable environmental factors to the player.

According to an embodiment herein, the monitoring device, the remote server, and the plurality of computing devices are connected through a communication network for establishing a wired and wireless communication. The communication network includes, but not limited to the Internet, an intranet, a radio-frequency network, telephonic network, a local area network (LAN), a wide area network (WAN), a proximity network such as Bluetooth, NFC, Wi-Fi, ZigBee, and Bluetooth Low Energy (BLE).

According to an embodiment herein, the gateway device is configured to enable a plurality of computing devices, to interface with the remote server. The gateway device is configured to communicate with the remote server and the plurality of computing devices through a plurality of communication protocols.

According to an embodiment herein, the plurality of sensors in the monitoring device is communicatively connected through wireless network to synchronize a capturing of information or data or an event of a physical motion. The plurality of sensors is configured to capture an information simultaneously. The plurality of sensors is configured to recreate an event from the synchronously captured information even when one of the sensors has failed to capture an event.

According to an embodiment herein, the artificial intelligence module is configured to automatically identify noise from detected and received information from the plurality of sensors and monitoring device. The artificial intelligence module is configured to contextually determine and identify noise from useful information. The artificial intelligence module is configured to generate an automated audio and text commentary of the physical motion, actions or poses that are captured using the system.

According to an embodiment herein, tic artificial intelligence module is configured to learn from the stored previous data or past data of historical data of the player to provide predictive analytics at a plurality of levels, and wherein the plurality of levels includes a player level analytics, a game level analytics and a session-level analytics, and wherein the artificial intelligence module is configured to predict the common mistakes or errors made by the player based on the analysis of past or previous games to provide a recommendation to help the player to overcome or avoid the errors in the game on action, and wherein the artificial intelligence module is configured to provide recommendations to enhance skill and performance of the player.

According to an embodiment herein, the plurality of end-point devices is configured to communicate with the remote server. The plurality of end-point devices is configured to analyze the stored past data of physical actions, poses or motion of a user and quantitatively analyze the physical actions, by comparing the preset or observed data from the same user or a plurality of other users or with a reference data stored and archived in the database.

According to an embodiment herein, the system further comprises a user interface for displaying analysis, visuals and results computed by the remote server. The user interface is configured to display a plurality of information of the player and the game. The plurality of information displayed on the user computing device through the user interface include a visual playback of the previous shots played by the player, analysis and visualization of the previous shots played by the player, analysis and visualization of the previous games played by the player, comparative analysis of the game and shots of the player with a plurality of other players.

According to an embodiment herein, the remote server is configured to provide connectivity with a plurality of computing devices for establishing inter-channel communication, and wherein the plurality of computing devices include a computing device of a player, a computing device of a coach and a computing device of a physician, and wherein the computing device of the player is connected to the computing devices of the coach and the computing device of the physician to enable the player to receive personal counseling from the physician and coach based on a complete analysis of the player and a game data of the player, and wherein the remote server is configured to enable the users/players for sharing the analyzed data and results to third-party networks, and wherein the third party networks is a social networking sites.

According to an embodiment herein, the monitoring device further comprises an impact sensor module. The impact sensor module is configured to detect and determine an impact of a ball on a bat. The impact sensor module is configured to determine a position of a plurality of sensors that is attached to the bat, the ball and a human user.

According to an embodiment herein, the plurality of end-point devices are configured to simulate a virtual rendering of a real-world human action, based on the output of the impact sensor module and the plurality of sensors in the monitoring device. The plurality of end-point devices are configured to enable an integrated rendering of the simulated virtual rendering and real-world human actions.

According to an embodiment herein, a microphone module is provided on the bat used by a player. The microphone module is connected to the communication module. The microphone module is configured to transmit an audio information related to the impact of bat with other player accessories.

According to an embodiment herein, a method is provided for monitoring and analyzing a game involving a ball and a bat. The method involves mounting a plurality of game monitoring devices on the bat of a player, sportswear, sports equipment and accessories used by a player. The plurality of monitoring devices is paired with a computing device of the player for providing an analysis report, feedback and recommendation based on the monitored game data and analysis of the collected data from the plurality of game monitoring devices. The time and clock in the plurality of game monitoring devices are synchronized to remove latency. A pitch calibration and a calibration of the plurality of sensors in the game monitoring devices are performed. A plurality of data regarding a game played by the player is collected with the game monitoring is collected. The collected data are transmitted to the paired computing device. The collected data are analyzed with an algorithm down loaded and installed in the paired computing device. The output data from the plurality of sensors are processed to generate a visual simulation of the actions captured by the monitoring device without using any video recording equipment. The output data from the monitoring device is contextually rendered in a plurality of end-point computing devices based on preset rules.

According to an embodiment herein, the plurality of data points or parameters captured by the plurality of sensors include a motion of the player, a speed at which the player has hit the ball, an angular motion and a direction of the shot.

According to an embodiment herein, the unwanted noise signals received from the plurality of sensors are filtered in the monitoring device.

According to an embodiment herein, an action and performance of the player is compared with a reference template of best or practices or ways of performing the physical motion, action or pose, based on preset rules and predetermined techniques, to provide a feedback to the player for improving a performance of the player, and to detect data points and processes the output signals to derive a pattern. A guidance on necessary changes or improvements needed to reach to the level of standard/template shots, is provided and wherein the guidance and analysis information is provided in a plurality of segments with a color coding for enhanced analysis According to an embodiment herein, the output data from the monitoring device are analyzed in a plurality of endpoint computing devices based on preset parameters, and wherein the preset parameters for analysis includes a position of the bat, a direction of the shot, a type of the shot, a swing analysis, a shot analysis, a direction analysis, a pressure analysis, a pattern determination, a length of the bowling delivery and a comparative analysis, a virtual replay of the game, and a mechanics of the game.

According to an embodiment herein, analysis of each shot is combined to derive analysis report for each delivery, game, session, and player. A plurality of game patterns of the player is combined to derive optimum factors or parameters for the player. The optimum factors or parameters for the player includes a body dynamics of the player relative to the bat position at the time of impact for increasing a game performance, and unfavorable environmental factors to the player.

According to an embodiment herein, a capturing of information or data or an event or a physical motion, the plurality of sensors in the monitoring device is synchronized to capture an information of an event simultaneously. An event is recreated from the synchronously captured information even when one of the sensors has failed to capture an event.

According to an embodiment herein, an automated audio and text commentary of the physical motion, actions or poses that are captured, is generated.

According to an embodiment herein, the stored previous data or past data of historical data of the player is processed to provide predictive analytics at a plurality of levels, and wherein the plurality of levels includes a player level analytics, a game level analytics, and a match level analytics. The predictive analytics is performed to predict the common mistakes or errors made by the player based on the analysis of past or previous games to provide a recommendation to help the player to overcome or avoid the errors in the game on action. The recommendations are provided to enhance skill and performance of the player.

According to an embodiment herein, the computed analysis, visuals and results are displayed with a user interface. A plurality of information of the player and the game is displayed on the user interface. The plurality of information displayed on the user computing device through the user interface includes a visual playback of the previous shots played by the player, analysis and visualization of the previous shots played by the player, analysis and visualization of the previous games played by the player, comparative analysis of the game and shots of the player with a plurality of other players.

According to an embodiment herein, an impact of a ball on a bat is detected and determined with the impact sensor module.

According to an embodiment herein, a common platform is provided for a plurality of coaches and players to share actionable insights and create a ranking of each player.

According to an embodiment herein, motion is captured using inertial measurement unit. The motion data from accelerometer, gyroscope and magnetometer are combined and integrated. The combined data is provided to a gaming engine for performing post noise filtering and error correction to recreate the motion in 3D visual space with the help of data points.

According to an embodiment herein, the common parameters collected and analyzed for cricket, hockey, tennis, ball badminton, and table tennis, are Quatranions, Linear Acceleration in all the 3 axis, Angular Velocity, Rotational Parameters (Roll, Pitch & Yaw).

According to an embodiment herein, the following parameters are adjusted to provide analysis depending upon the selected game. The parameters include a Device Location, Impact Threshold, Visual Context & Background, Scorecard List:

According to an embodiment herein, the parameter involving axis orientation are adjusted according to the selected game based on the placement and orientation of device on sports equipment. This involves mapping of x, y & z axis of the device world to that of game world. Device location is also used to accurately determine the speed.

According to an embodiment herein, threshold parameter is adjusted to capture the point of impact based on the game type. Key parameter for this impact determination is acceleration and rate of change of acceleration.

According to an embodiment herein, the visual simulation of motion including player, ground/court/equipment is altered based on parameter mapping depending upon the selected game.

According to an embodiment herein, a list of key items for scorecard are displayed on a Scorecard List based upon the game. The list includes swing speed, impact parameter, angle of bat, balance index, etc.

FIG. 1 illustrates a block diagram of a system for monitoring and analyzing sports performance of a player, according to one embodiment herein. The system includes a game monitoring device/s 102, a gateway device 105, a communication network 104, a remote server 106, and a computing device 116. The remote server comprises a plurality of modules including, but not limited to a filtering and signal processing module 108, an analytics module 110, a database 112, a social media module, a gaming engine 119, and an artificial intelligence module 114. The computing device 116 includes a plurality of modules along with a user interface 118, and in an embodiment, a gaming engine 119. The embodiment comprises a machine learning module 120, which is configured to identify patterns from the observed data and provide contextual suggestions on the user's computing device.

The game monitoring device/s 102 detects a plurality of data points from the player or game devices and transmits the same to the remote server 106 through the gateway device 105. The remote server 106 filters and processes the signals and analyses each shot and the game of the player. The analysis is visualized and is displayed/rendered on the computing device 116 of a user. The game monitoring device/s 102, the remote server 106, and the computing device communicate with each other using the communication network 104.

The game monitoring device/s 102 comprises a plurality of sensors, for detecting a plurality of data points from the player involved in a game or game devices. The game monitoring device/s 102 is a hardware device that is placed in the vicinity of the player or is worn by the player as an accessory or on the sports equipment used in the given sports or embedded inside the sports equipment or accessories. For example, the game monitoring device/s is placed as a wristband for a player practicing a cricket game. According to an embodiment herein, the game monitoring device/s 102 is placed on one of the accessories worn by the player. For example, the game monitoring device/s is placed behind the helmet and/or on behind the cricket bat in a non-intrusive and non-obtrusive way and/or inside a cricket bat or ball, for a player practicing a cricket game.

The game monitoring device/s 102 includes a plurality of sensors for detecting the data points from the player. The examples of the sensors included in the game monitoring device/s are motion sensors, temperature sensors, pressure sensors, position sensors, proximity sensors, speed sensors, an audio sensor, a pyroelectric sensor, piezoelectric sensor and the like. Further, the game monitoring device/s 102 also includes a transceiver for transmitting the received data points to a remote computing device. Further, the game monitoring device/s 102 is provided with a filler circuit to filter the noise signals and unwanted spurious signals and noises from the detected data points and process the signals to derive a pattern. Further, the game monitoring device/s ensures a synchronization of the plurality of sensors so that the plurality of data points received from the plurality of sensors are translated to meaningful and aligned game insights for a same event or action or game.

The gateway device 105 is a device that interfaces with other computing devices and the remote server 106. According to an embodiment herein, the gateway device 105 is referred as a computing device such as a laptop, desktop computer, smart phone, and the like that is configured to perform the tasks of a gateway. The gateway device 105 is configured to communicate with the remote server 106 and the other computing devices using a plurality of protocols.

A communication is established between the game monitoring device/s 102, the remote server 106, and the computing device 116 through the communication network 104. The communication network includes both a wired and wireless communication. The examples of the communication network include, but ate not limited to the Internet, an intranet, a radio-frequency network, telephonic network, a local area network (LAN), a wide area network (WAN), a proximity network such as Bluetooth, NFC, Wi-Fi, ZigBee, and Bluetooth Low Energy (BLE).

The remote server 106 is configured and programmed to receive the detected signals, process the detected signals and derive analysis about a shot, an action, a pose a style of play, a movement and a game of the player in action. The filtering and signal processing module 108 is configured to filter the unwanted noise signals received from the plurality of the sensors of the game device 102. The filtering and signal processing is carried out using the standard methods known to the person skilled in the art.

The analytics module 108 is configured to analyze the processed signals at a plurality of levels. The analysis module 108 is configured to analyze the processed signals based on the pre-determined steps used for analysis. For example, the analysis for the game of cricket include, but are not limited to position of the bat, virtually replay of the game, the mechanics of the game, the direction of the shot, the type of the shot, swing analysis, shot analysis, direction analysis, pressure analysis, pattern determination, length of the bowling delivery and comparative analysis. This analysis also provides a comparison with the best practice/template shots including guidance on necessary changes or improvements needed to reach to the level of standard/template shots. Information is provided in various segments with color coding for enhanced analysis.

The analysis module 108 is further configured to combines analysis of each shot and derive analysis for each delivery, game, session user, and the like. Further, the analysis module 108 is configured to combine multiple game patterns of the player and derive further analysis such as the optimum factors like body dynamics relative to the bat position at the time of impact for the player to play well, the unfavorable environmental factors to the player and the like.

The database 110 is provided for storing the user data, data related to the analysis, and meta-data of the overall system, and the like. The database 110 is further used for storing information related to players, coaches, data used for feeding the analysis module and the like.

The artificial intelligence module 114 is configured to derive data from the already stored data to provide a predictive analytics at various levels such as at player level, game level, and match level. For example, the artificial intelligence module 114 is configured to predict the common mistakes the player would make based the analysis of his games and also provide a platform to help him/her to overcome it. Further, the artificial intelligence module 114 is configured to recommend improvements to enhance the player's capability/skill.

The monitoring and analyzing of a sports performance of a player is done at a user computing device 116. The remote server renders the analysis and the player's details on the computing device 116. According to an embodiment herein, the computing device 116 receives the information from the remote server 106 through the communication network 104. The examples of the computing device 116 include, but are not limited to a smartphone, a laptop, a wearable device, a smart television, a tablet computer, and the like.

The user interface 118 is provided at a front-end of the system for displaying analysis, visuals and results computed by the remote server. Further, the user interlace 118 is provided with machine-readable instructions. The user interface 118 is configured to display a plurality of data related to the player and the game. The information displayed on the computing device 116 through the user interface 118 include, but are not limited to the visual playback of the previous shot played, analysis and visualization of the previous shot, analysis and visualization of the previous game, comparative analysis with a plurality of other players, and the like.

According to an embodiment herein, the remote server 106 is communicatively connected to a plurality of other computing devices for establishing inter-channel communication. For example, a player A is connected to a coach B and also a physician C, to enable the player A to receive a mentoring on various fronts. It is possible for the coach B and the physician C to get connected to the player A to provide a personal counselling as they are provided with the complete analysis of the player A and his game data. Further, the remote server 106 is configured to enable the users to share the analyzed data and results to third-party networks such as social networking sites. The remote server 106 enables the sharing the analyzed data using a social media module (not shown in the figure).

Figure 2:
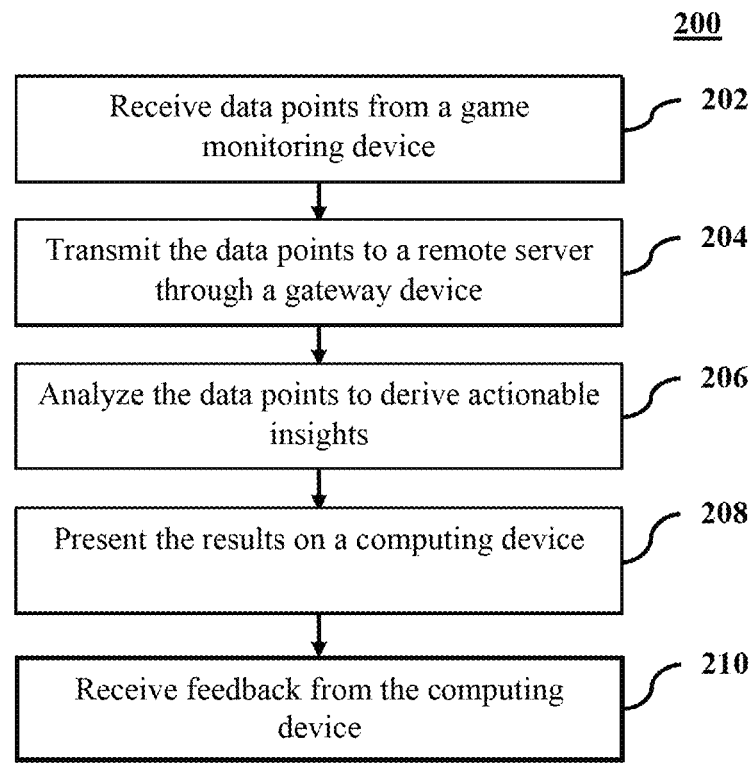
FIG. 2 illustrates a flowchart explaining a method for monitoring and analyzing sports performance of a player, according to one embodiment herein.

FIG. 2 illustrates a flowchart explaining a method for monitoring and analyzing sports performance of a player, according to one embodiment herein. The player is provided with a user computing device connected to the plurality of game monitoring device/s for receiving the plurality of data collected by the plurality of the game monitoring devices. The user computing device is connected to a portal or software for analyzing his performance at various levels. The player accesses the portal in various ways, including but not limited to a mobile application, a web application, a browser-based application, a software plugin, a standalone application, and a third-party supported application.

According to an embodiment herein, the user has the option to register into the portal as different types of operators, such as a player, a physician, a sports scientist, a coach, and the like. At first, the remote server receives a plurality of data points from the game monitoring device/s (Step 202). The game monitoring device/s receives the plurality of data points from a plurality of the sources including, but not limited to a plurality of sensors included in the game monitoring device/s. The plurality of data points received from other components, accessories of the game include a communicable wicket, a communicable crease, and the like. Further, the game monitoring device is configured to transmit the received data points to a game monitoring device for filtering and processing (Step 204). The game monitoring device is configured to transmit the data points to the remote server through the communication network through the gateway device. According to an embodiment herein, the game monitoring device is also configured to transmit the received data points to the computing device.

Once the remote server receives the data points from the game monitoring device/s, the data points are analyzed and an actionable insight regarding the shot, game, player are derived (Step 206). According to an embodiment herein, the analysis also includes predictive analysis using artificial intelligence for predicting possible mistakes the player might make and also recommends effective ways to minimize those errors.

The analyzed results are then presented to the user on the computing device through the communication network (Step 208). The analysis and results are presented to the user in a plurality of ways, which include but not limited to the graphical representation, tabular representation, statistical representation and textual representation.

Further, the monitoring and analysis system provides the users and third-party service providers (including by not limited to the services offered through social media channel) to provide feedback about the player's techniques, suggest improvements, rate the game, compete with other players in virtually simulated games, challenge other players, and the like. These are received by the remote server and is further utilized for improving analysis techniques (Step 210).

Figure 3:
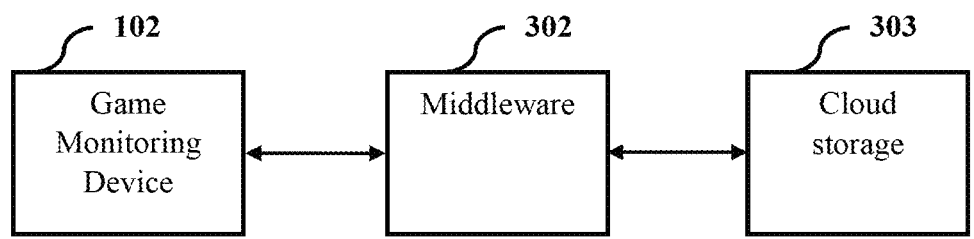
FIG. 3 illustrates a functional block diagram of a system for monitoring and analyzing sports performance, according to one embodiment herein.

FIG. 3 illustrates a functional block diagram of a system for monitoring and analyzing sports performance. The system comprises a game monitoring device 102, a middleware module 302 and a cloud storage module 303. The game monitoring device 102 is configured to measure and store information related to the performance of a player. The middleware module 302 is connected to the game monitoring device 102 through a wireless data transmission protocol. The middleware module 302 is configured to enable a user to access the information stored in the game monitoring device 102. The middleware module 302 is connected to the cloud storage module 303 through Internet. The cloud storage module 303 is configured to enable a user to perform analysis on the data stored in the game monitoring device 102 through machine learning techniques and data analytics methods.

Figure 4:
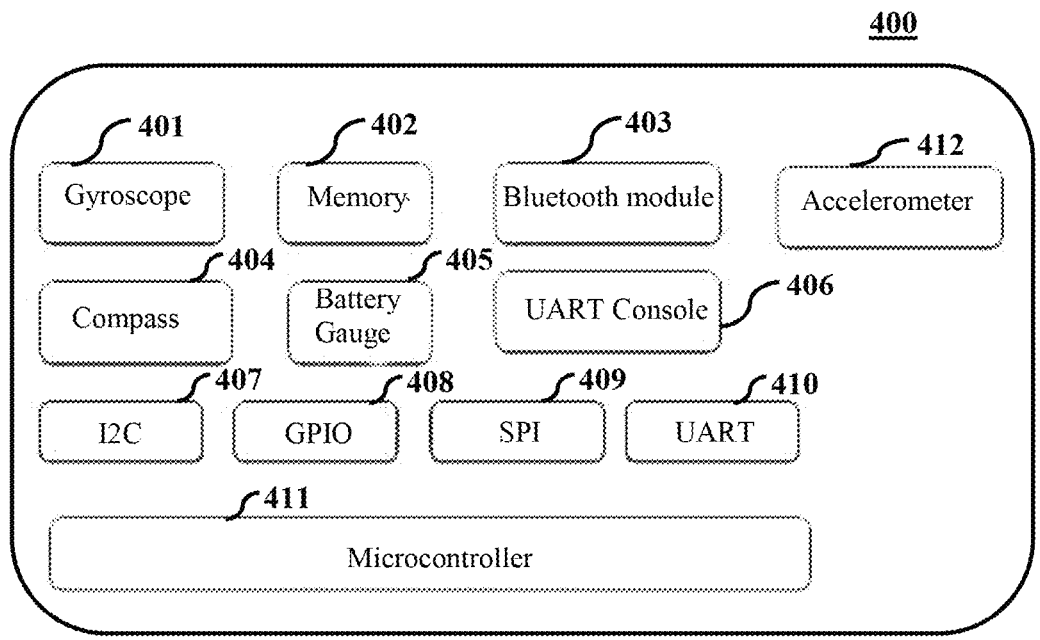
FIG. 4 illustrates a block diagram of a game monitoring device in a system for monitoring and analyzing sports performance, according to one embodiment herein.

FIG. 4 illustrates block diagram of a game monitoring device, according to one embodiment herein. The game monitoring device comprises a gyroscope module 401, a memory 402, a Bluetooth module 403, a compass module 404, a battery gauge 405, a UART console 406, an I²C module 407, a GPIO module 408, a SPI module 409, a UART module 410 and a microcontroller module 411, and an accelerometer 412. The device further comprises a physical switch module and a microphone module (not shown in the figure). The physical switch module is operated to power on and off the device, and also to change a mode of operation of the device.

Figure 5:
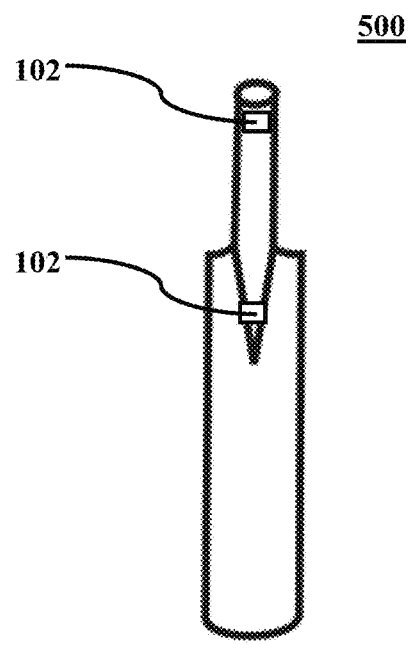
FIG. 5 illustrates a from view of a bat installed with a plurality of game monitoring devices on sports equipment in a system for monitoring and analyzing sports performance, according to one embodiment herein.

FIG. 5 illustrates a front view of a bat installed with a plurality of game monitoring devices on sports equipment in a system for monitoring and analyzing sports performance, according to one embodiment herein. With respect to FIG. 5, the game monitoring device 102 is installed respectively on a helmet, pad, and shoe worn by a player. Each game monitoring device comprises a sensor module, microprocessor, memory, microphone, battery for power supply, and a communication module. The sensor module comprises an accelerometer, gyroscope, magnetometer, compass, and inertial motion sensor. The sensor module is configured to collect the data during a gameplay and the collected data are analyzed at the microcontroller based on algorithm stored in the memory. The output of the analysis is transmitted to the paired user computing device for rendering the game and visual feedback to the player in real time or near real time for improving the performance. The player is provided with a prediction of a possible mistake one cam make based on past performance and the current play.

Figure 6:
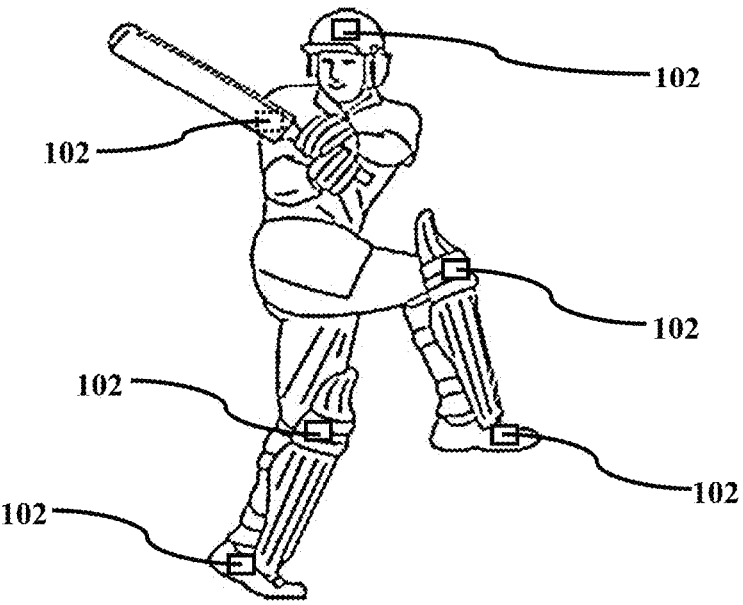
FIG. 6 illustrates a front view of a player with sports equipment and accessories installed with a plurality of game monitoring devices on sports equipment in a system for monitoring and analyzing sports performance, according to one embodiment herein.

FIG. 6 illustrates a front view of a player with sports equipment and accessories installed with a plurality of game monitoring devices on sports equipment in a sports activity such as cricket in a system for monitoring and analyzing sports performance, according to one embodiment herein. With respect to FIG. 6, the player illustrated is a batsman in the game of cricket, wherein the batsman holds a bat to hit the ball. The game monitoring device 102 is installed respectively on a handle portion and on the backside of the bat surface. Each game monitoring device comprises a sensor module, microprocessor, memory, microphone, battery for power supply, and a communication module. The sensor module comprises an accelerometer, gyroscope, magnetometer, compass, and inertial motion sensor. The sensor module is configured to collect the data during a game-play and the collected data are analyzed at the microcontroller based on algorithm stored in the memory. The output of the analysis is transmitted to the paired user computing device for rendering the game and visual feedback to the player in real time or near real time for improving the performance. The player is provided with a prediction of a possible mistake one cam make based on past performance and the current play.

Figure 7:
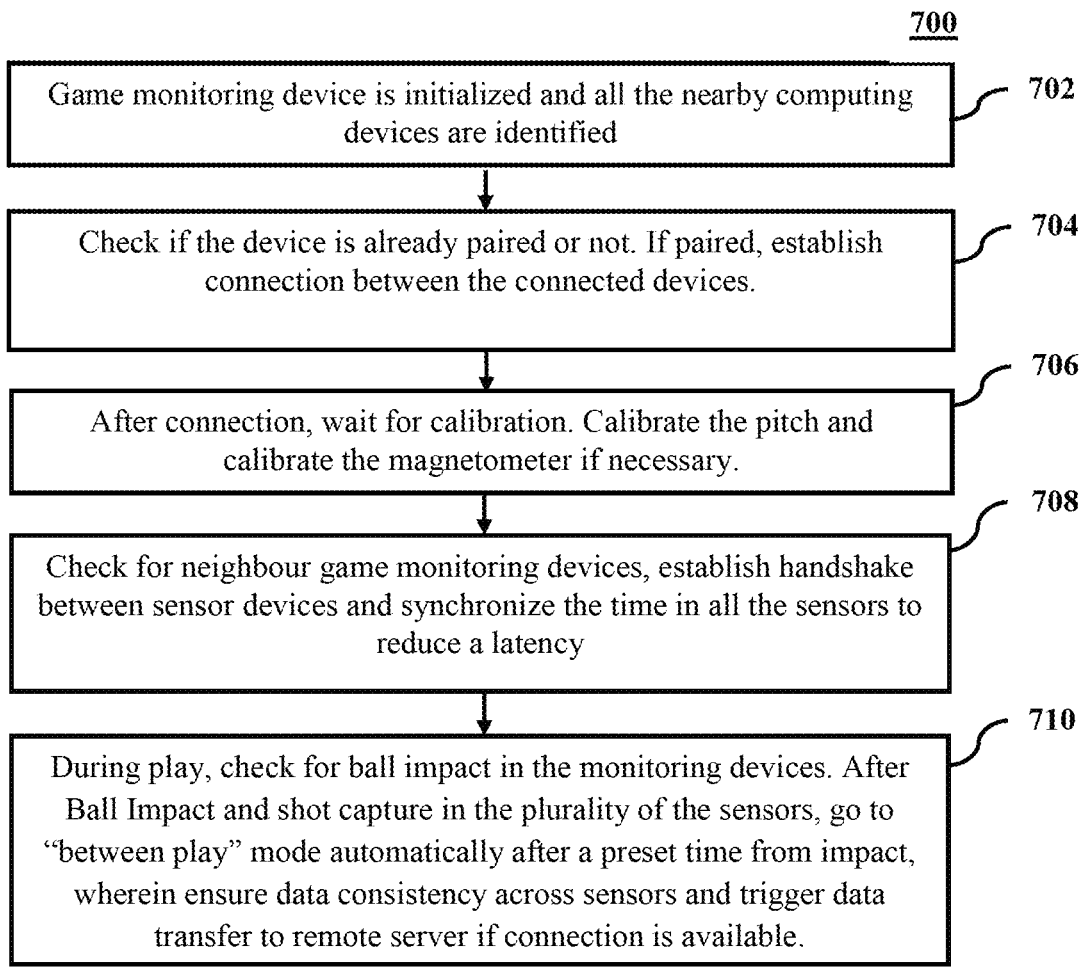
FIG. 7 illustrates a flow chart explaining a method for monitoring and analyzing sports performance, according to one embodiment herein.

FIG. 7 illustrates a flowchart explaining a method for monitoring and analyzing sports performance in a game such as cricket, according to one embodiment herein. The method comprises the following steps: Game monitoring device is initialized and all the nearby computing devices are identified (702). The pairing of the nearby computing device with the game monitoring device is checked. When the pairing of the nearby computing device with the game monitoring device is checked successfully, a communication is established between the paired devices. (704). After communicatively connecting the game monitoring device and a paired computing device, a calibration of the pitch and the calibration of the sensors are performed. The pitch is calibrated and the magnetometer is calibrated if necessary (706). The presence or availability of nearby game monitoring devices is checked to establish a handshake between the sensor devices and the clock/time in all the sensors are synchronized to reduce a latency (708). During play, a check for ball impact in the monitoring devices. After detection of ball impact and shot capture with the plurality of the sensors, select a "between play mode" automatically after a preset time from impact, to ensure data consistency across sensors to trigger data transfer to remote server when communication connection between the paired computing devices is available (710).

Figure 8:
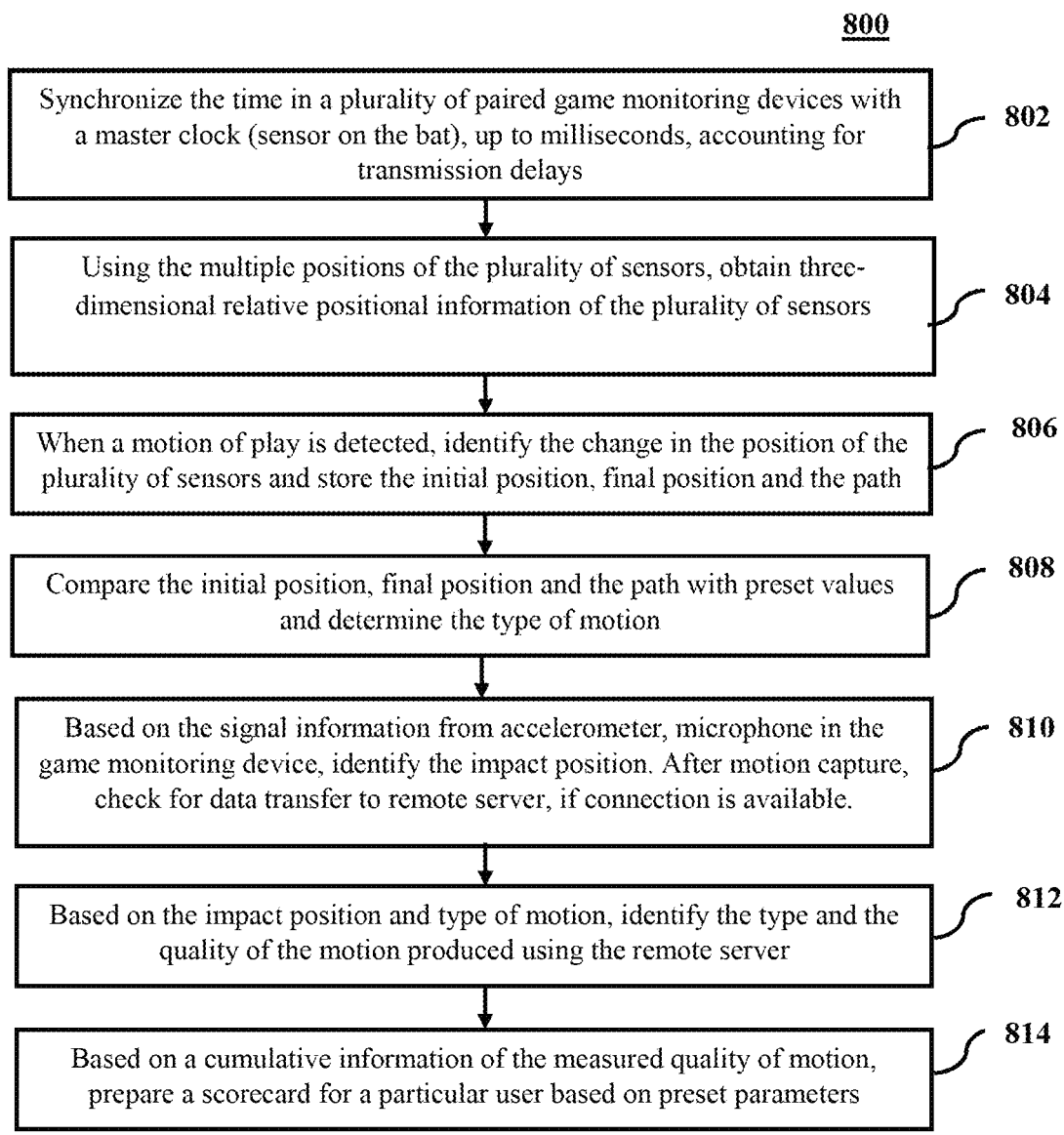
FIG. 8 illustrates a flow chart explaining a method for a calibration and determination of direction of motion of player and sports gear in a field of play, according to one embodiment herein.

FIG. 8 illustrates a flow chart explaining a method for a calibration, time synchronization of plurality of sensors and determination of direction of motion of player and sports gear in a field of play in a sports game such as cricket, according to one embodiment herein. The method comprises the following steps: The time or clock in a plurality of paired game monitoring devices is synchronized with a master clock (sensor on bat), up to milliseconds, accounting for transmission delays (802). Between the shots, the sensors continuously synchronize with each other to ensure that the local time is not drifting apart. A three-dimensional relative positional information of the plurality of sensors is obtained or acquired using the multiple positions of the plurality of sensors (804). When a motion of play is detected, by the sensor on the bat, the change in position of the plurality of sensors is identified to store the initial position, final position, impact position and the path (806). The initial position, final position, impact position and the path are compared with preset values in the remote server to determine a type of motion (808). Based on the signal information from accelerometer and microphone in the game monitoring device, the impact position is accurately identified. After capturing the motion data, a data transfer to remote server is checked, if connection is available. (810). Based on the impact position and type of motion, the type and the quality of the movement/motion of player is identified in the remote server (812). Based on a cumulative information of the measured quality of motion, a scorecard is prepared for a particular user based on preset parameters (814). The score card comprises swing speed, impact speed, lifting angle of bat, and a balance index.

Figure 9:
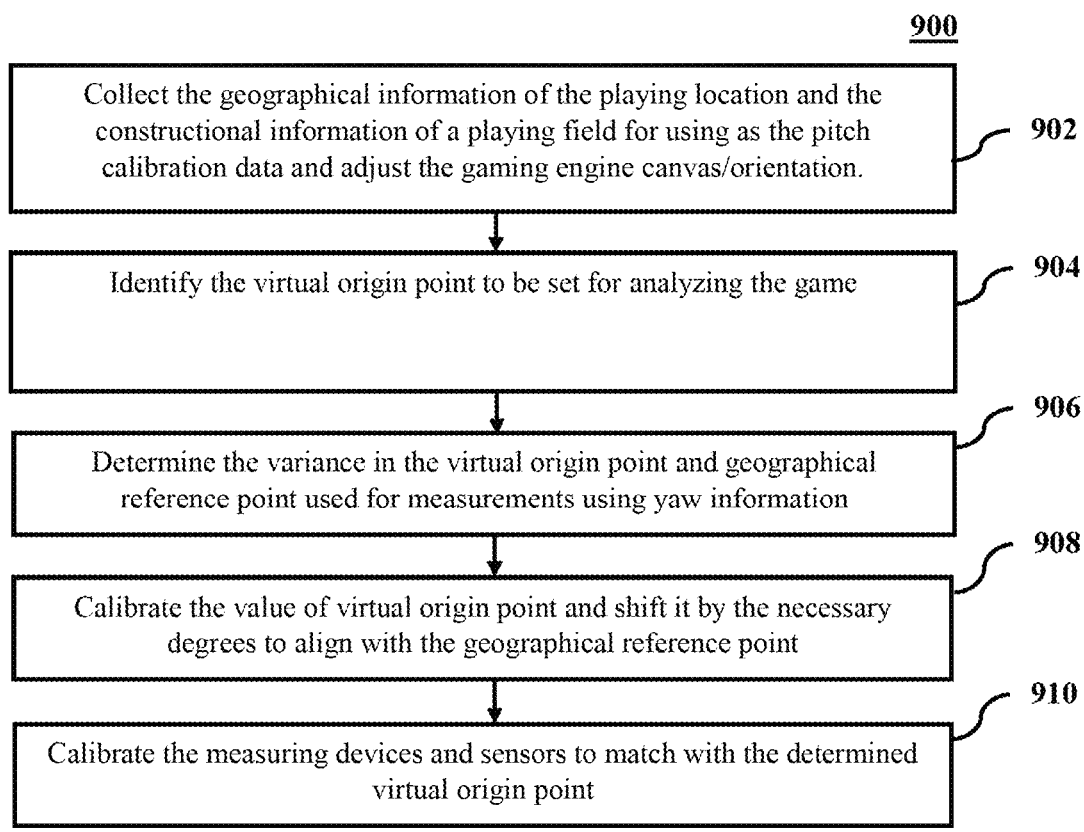
FIG. 9 illustrates a flow chart explaining a method for calibration of a field of play for enabling monitoring and analyzing the performance of a player, according to one embodiment herein.

FIG. 9 illustrates a flow chart explaining a method for using calibration of a field of play for monitoring and analyzing the performance of a player in a sports game such as cricket in a remote server, according to one embodiment herein. The method comprises the following steps: the geographical information of the playing location and the constructional information of a playing field are collected and used as a pitch calibration data for calibrating a playground. Then the gaming engine canvas/orientation is adjusted using the collected pitch calibration data (902). The virtual origin point to be set for analyzing the game is identified (904). The variance in the virtual origin point and geographical reference point used for measurements is determined based on yaw data (906). The value of virtual origin point is calibrated and shifted by the necessary degrees to align with the geographical reference point (908). The measuring devices and sensors are calibrated to match with the determined virtual origin point (910).

Figure 10:
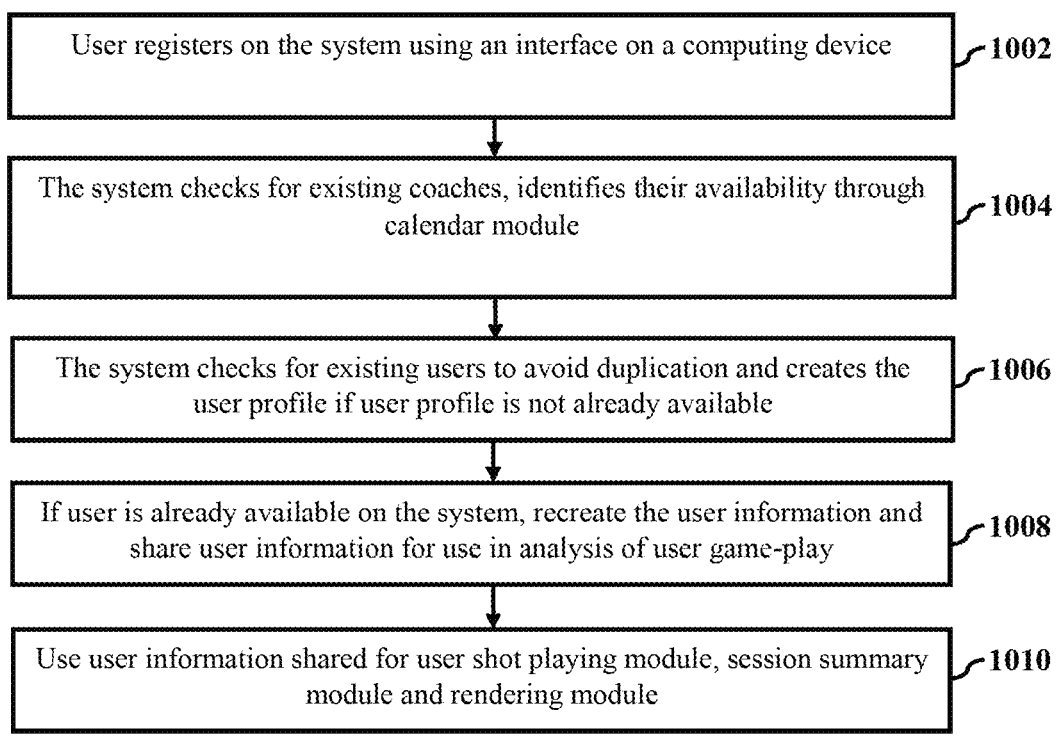
FIG. 10 illustrates a flow diagram for management of a user in a system for monitoring and analyzing the performance of a player, according to one embodiment herein.

FIG. 10 illustrates a flow chart explaining a method of management of a user in a system for monitoring and analyzing the performance of a player, according to one embodiment herein. The method comprises the following steps: user registers on the system using an interface on a computing device (1002); the system checks for existing coaches, identifies their availability through calendar module (1004); the system checks for existing users to avoid duplication and creates the user profile if user profile is not already available (1006); if user is already available on the system, recreate the user information and share user information for use in analysis of user game-play (1008); and, use user information shared for user shot playing module, session summary module and rendering module (1010).

Figure 11:
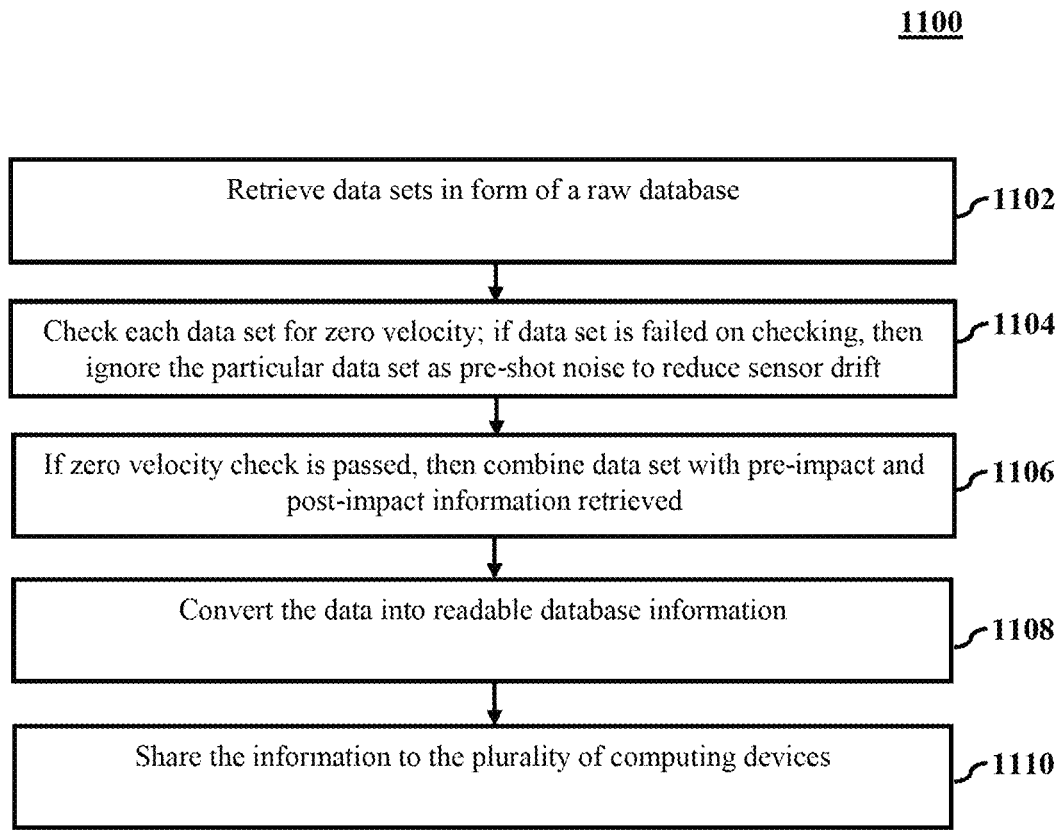
FIG. 11 illustrates a flow diagram for filtration of data to be rendered and used in monitoring and analyzing the performance of a player, according to one embodiment herein.

FIG. 11 illustrates a flow chart explaining a method for filtering the data to be rendered and used in monitoring and analyzing the performance of a player in a system for monitoring and analyzing the performance of a player, according to one embodiment herein. The method comprises the following steps: the data sets are retrieved from a raw database (1102). Each data set is checked for zero velocity to reduce the time window before and after a ball impact so that linear drift is drastically reduced. When the data set is failed in a zero velocity check, then the particular data set is ignored as pre-shot noise (1104). When the data set is passed successfully in a zero velocity check, then the data set is combined with the retrieved pre-impact information and a post-impact information (1106). The combined data is converted into readable database information (1108). The converted readable data base information is shared with a plurality of computing devices (1110).

Figure 12:
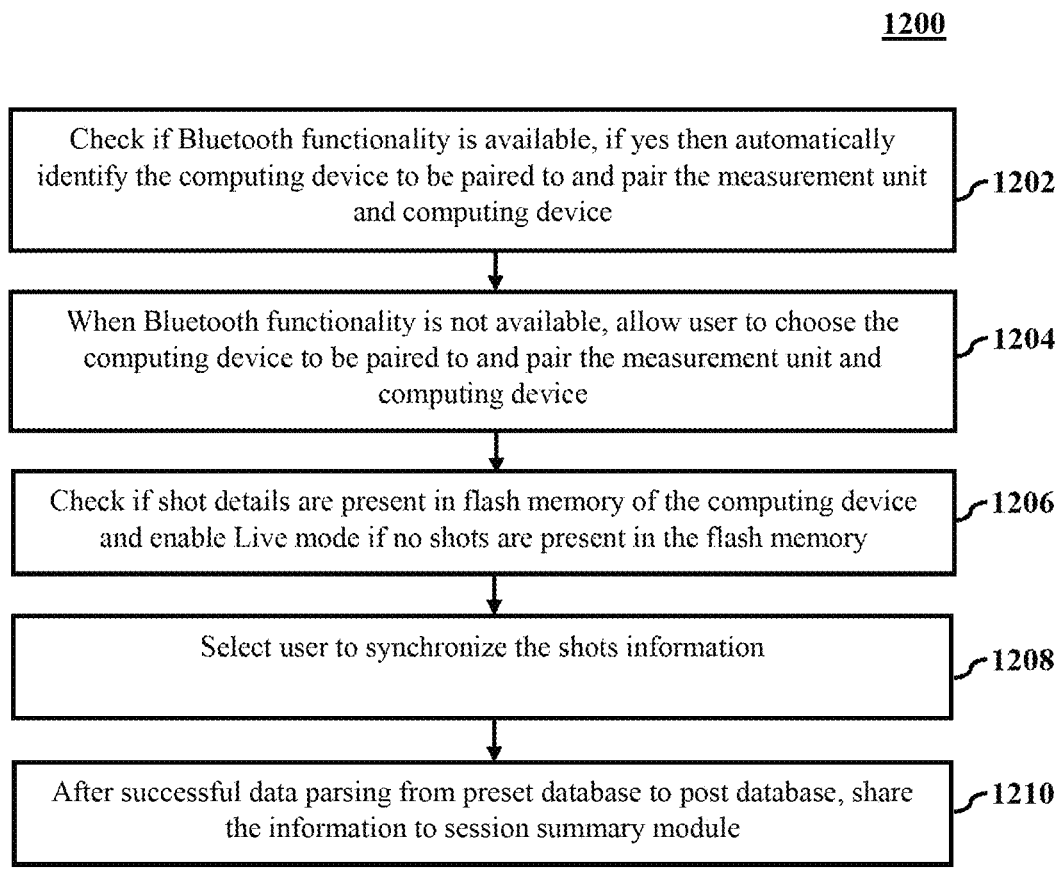
FIG. 12 illustrates a flow diagram for data communication using Bluetooth in a system for monitoring and analyzing the performance of a player, according to one embodiment herein.

FIG. 12 illustrates a flow chart explaining a method for establishing a data communication using Bluetooth in a system for monitoring and analyzing the performance of a player, according to an embodiment herein. The method comprises the following steps: the availability of a Bluetooth communication is checked. When the availability of a Bluetooth communication is identified, the computing device to be paired is automatically identified to pair the measurement unit/monitoring device and the computing device (1202). When the Bluetooth communication is not available, then user is allowed to choose the computing device to be paired to pair the measurement unit and computing device (1204). The presence of shot details in flash memory of the computing device is checked. A Live mode of data transfer is enabled, when no shot details are present in the flash memory (1206). The user is selected for synchronizing the shot details (1208). After successful parsing of data from preset database to Json file format, the parsed information is shared to session summary module (1210).

Figure 13:
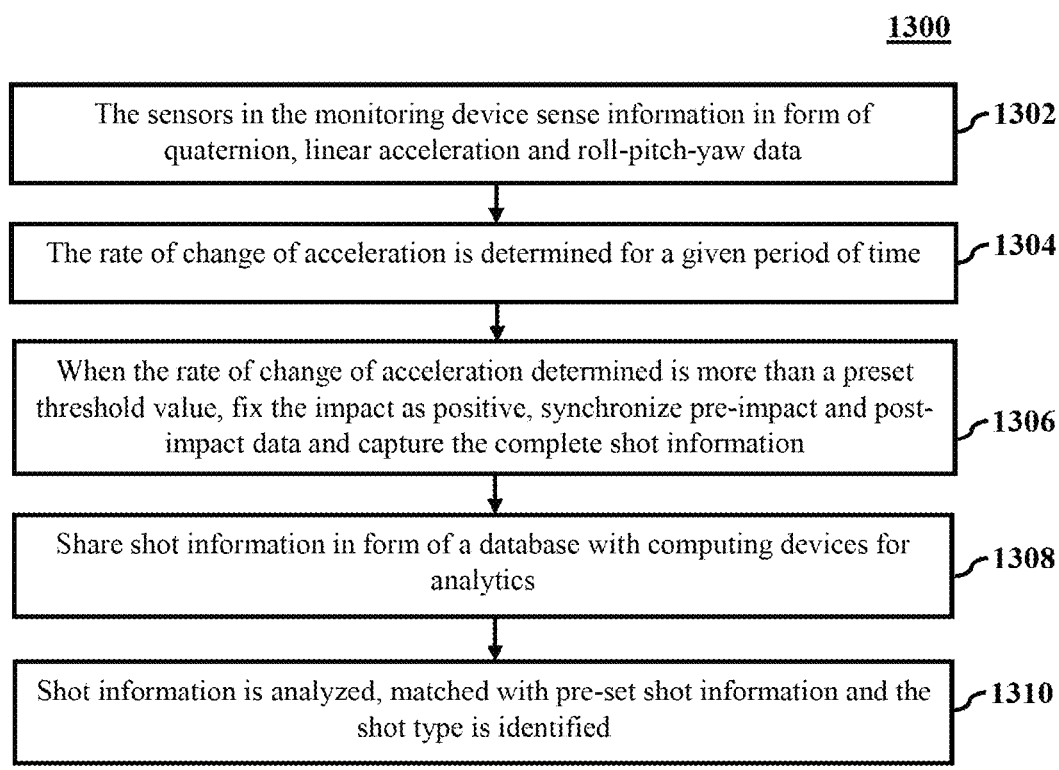
FIG. 13 illustrates a flow chart explaining a method for determining an impact between two sporting equipments in a system for monitoring and analyzing the performance of a player, according to one embodiment herein.

FIG. 13 illustrates a flow diagram for determining a ball impact position and data in a system for monitoring and analyzing the performance of a player. The method comprises the following steps: the sensors in the monitoring device sense information in form of quaternion, linear motion such as linear acceleration and rate of change acceleration, and angular motion such as roll-pitch-yaw data (1302). The linear motion is derived from acceleration by performing double integration the sensor data over time. The linear acceleration at three different levels or rates are observed to identify the ball impact area. Then the rate of change of acceleration and the interrupts are used to accurately identify a ball impact instance. The ball impact position is further fine-tuned with the audio data from microphone to remove the noise signals to accurately identifying the ball impact position by removing the inherent drift of the motion sensors. The rate of change of acceleration is determined for a given period of time. (1304). When the estimated rate of change of acceleration is more than a preset threshold value, then the impact is considered as a positive impact. The retrieved pre-impact data and post-impact data is integrated to capture the complete shot information (1306). The shot information or details from the database is shared with computing devices for analytics (1308). The shot information/details is analyzed, matched with preset shot information/details to identify a type of shot played by the player (1310).

According to an embodiment herein, a ball impact area is identified from the plurality of sample data collected with the motion sensors using the linear acceleration. The linear motion is derived from acceleration by performing a doable integration the sensor data over time. To manage the inherent motion drift resulting from the use of motion sensors and the above approach, the time window of motion capture is reduced by accurately identifying instants of time at which the motion starts and ends. The thresholds of the above are derived from numerous data sets acquired from the sensors.

According to an embodiment herein, the rate of change of acceleration data is used to accurately identify the ball impact area accurately. The interrupts like that of "double tap" from accelerometer is further used to triangulate on exact ball impact sample. The microphone data is used as further additional input to detect accurate ball impact position. The quaternions and Roll, Pitch and Yaw is further used to understand the angular motion of the bat and is used by the gaming engine to show the angular movement of the bat.

Figure 14:
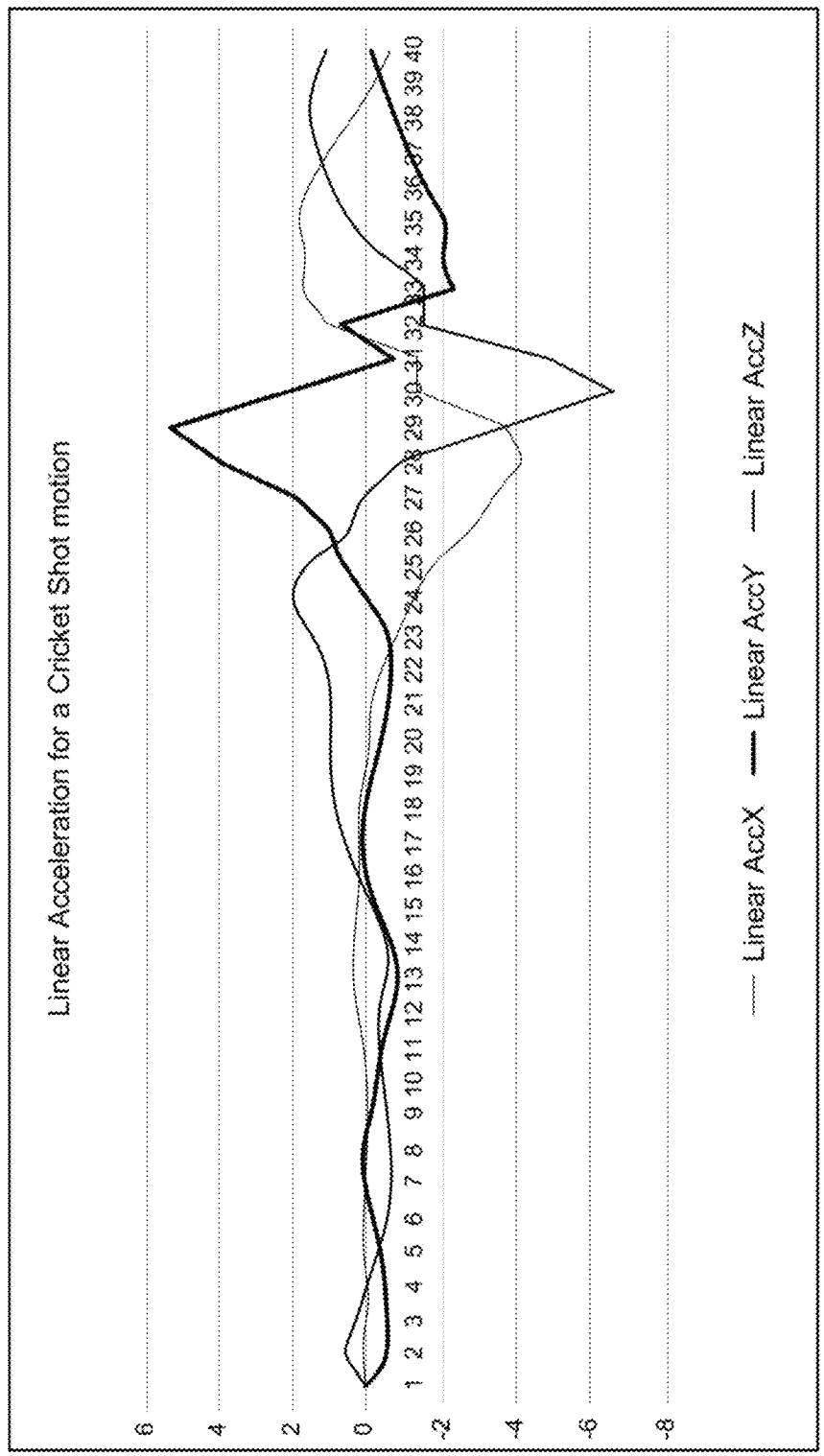
FIG. 14 illustrates a chart indicating an exemplary representation of an analysis for determining linear acceleration for a cricket shot motion using a system for monitoring and analyzing the performance of a player, according to one embodiment herein.

FIG. 14 illustrates a chart indicating an exemplary representation of an analysis for determining linear acceleration for a cricket shot motion using a system for monitoring and analyzing the performance of a player, according to one embodiment herein. The linear motion is derived from acceleration by performing double integration the sensor data over time. The linear acceleration data collected at three different axes are plotted on graph. The linear motion data helps in identifying the linear trajectory of the movement of plurality of the sensors for investigation and analysis. The inherent motion drift resulting from the use of motion sensors is compensated by reducing the time window of motion capture by accurately identifying instants of time at which the motion starts and ends, the thresholds of the above are derived from numerous data sets acquired from the sensors.

Figure 15:
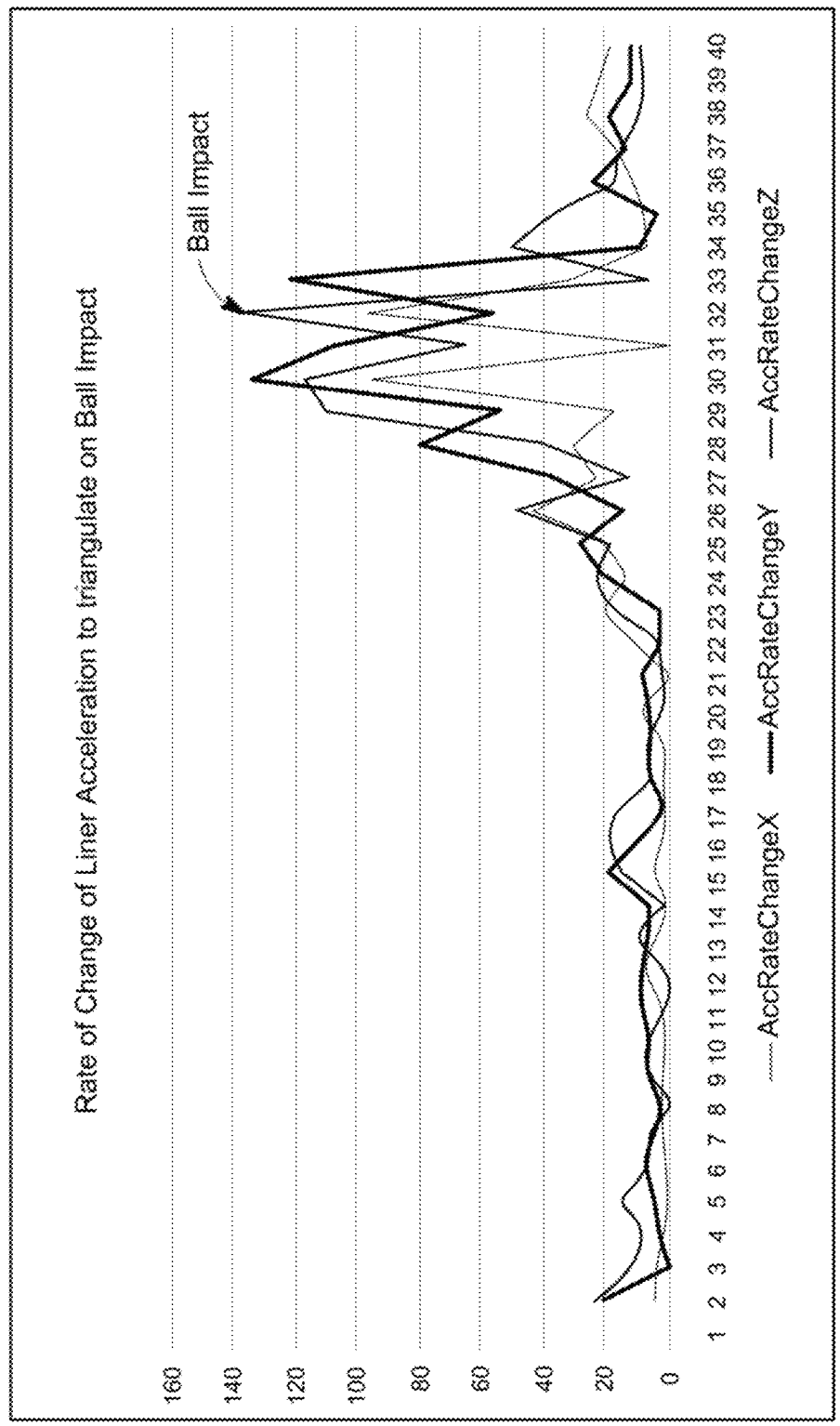
FIG. 15 illustrates a chart indicating an exemplary representation of an analysis for determining rate of change of linear acceleration for a cricket shot motion using a system for monitoring and analyzing the performance of a player, according to one embodiment herein.

FIG. 15 illustrates a chart indicating in exemplary representation of an analysis for determining an absolute rate of change of linear acceleration for a cricket shot motion using a system for monitoring and analyzing the performance of a player, according to one embodiment herein. The absolute rate of change of linear acceleration is utilized to triangulate the impact of a ball on a bat, by analyzing the change of linear acceleration in all three axes. The absolute rate of change linear acceleration is used to identify a ball impact position accurately to collect a pre impact data and a post impact data. The absolute rates of change of acceleration at three different axes with respect to a sample data is plotted on a chart. When the estimated absolute rate of change of acceleration is more than a preset threshold value, then the impact is considered as a positive impact. The accelerometer interrupts are used to further triangulate the ball impact position. The retrieved pre-impact linear acceleration data and post-impact linear acceleration data is integrated to capture the complete shot information. The shot information or details from the database is shared with computing devices for analytics. The shot information/details is analyzed, matched with preset shot information/details to identify a type of shot played by the player.

Figure 16:
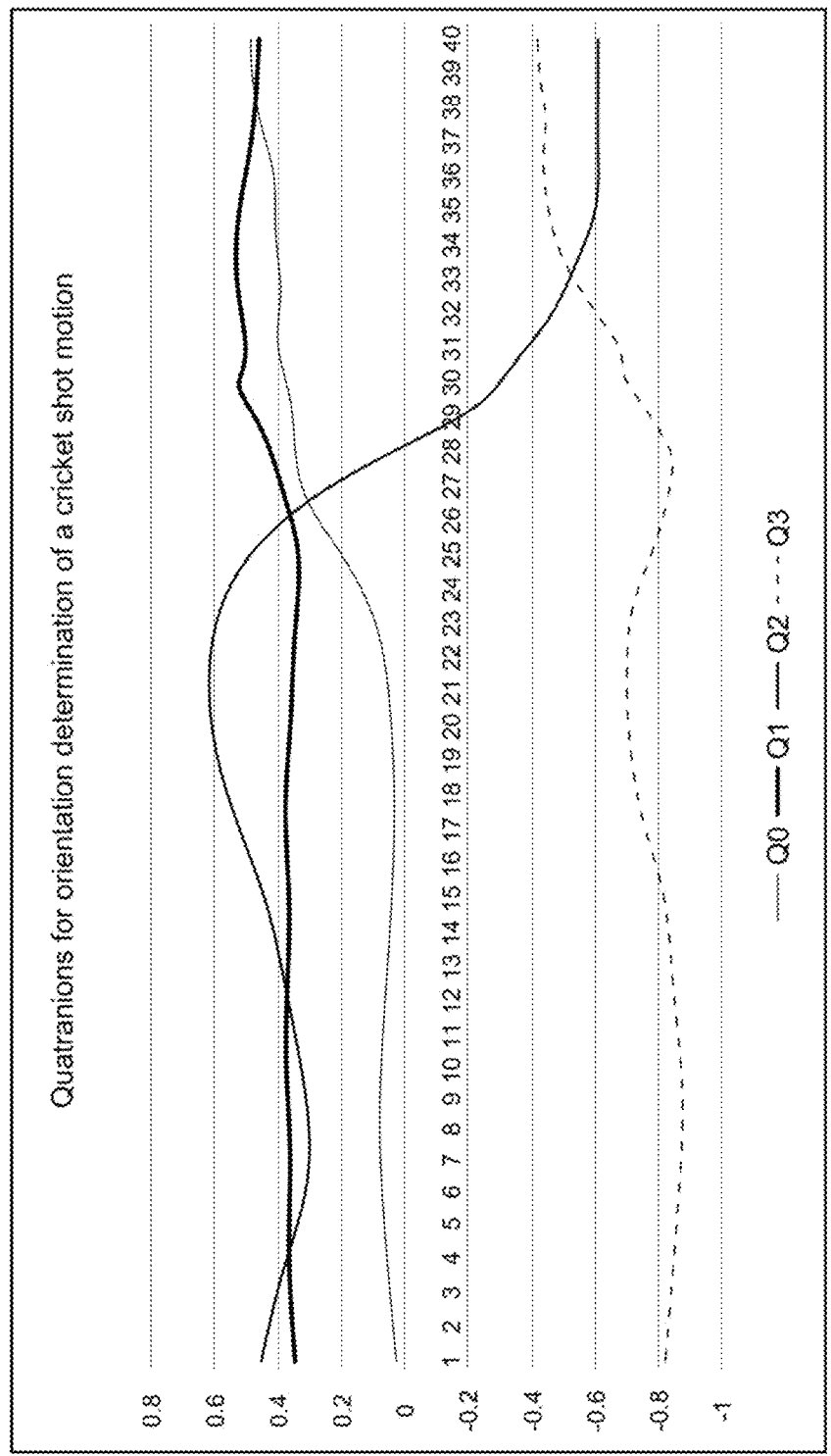
FIG. 16 illustrates a chart indicating an exemplary representation of an analysis of quaternions for determining an orientation of a cricket shot motion using a system for monitoring and analyzing the performance of a player, according to one embodiment herein.

FIG. 16 illustrates a chart indicating an exemplary representation of an analysis of quaternions for determining an orientation of a cricket shot motion using a system for monitoring and analyzing the performance of a player, according to one embodiment herein. The quaternions provide a convenient mathematical notation for representing orientations and rotations of objects in three dimensions.

Figure 17:
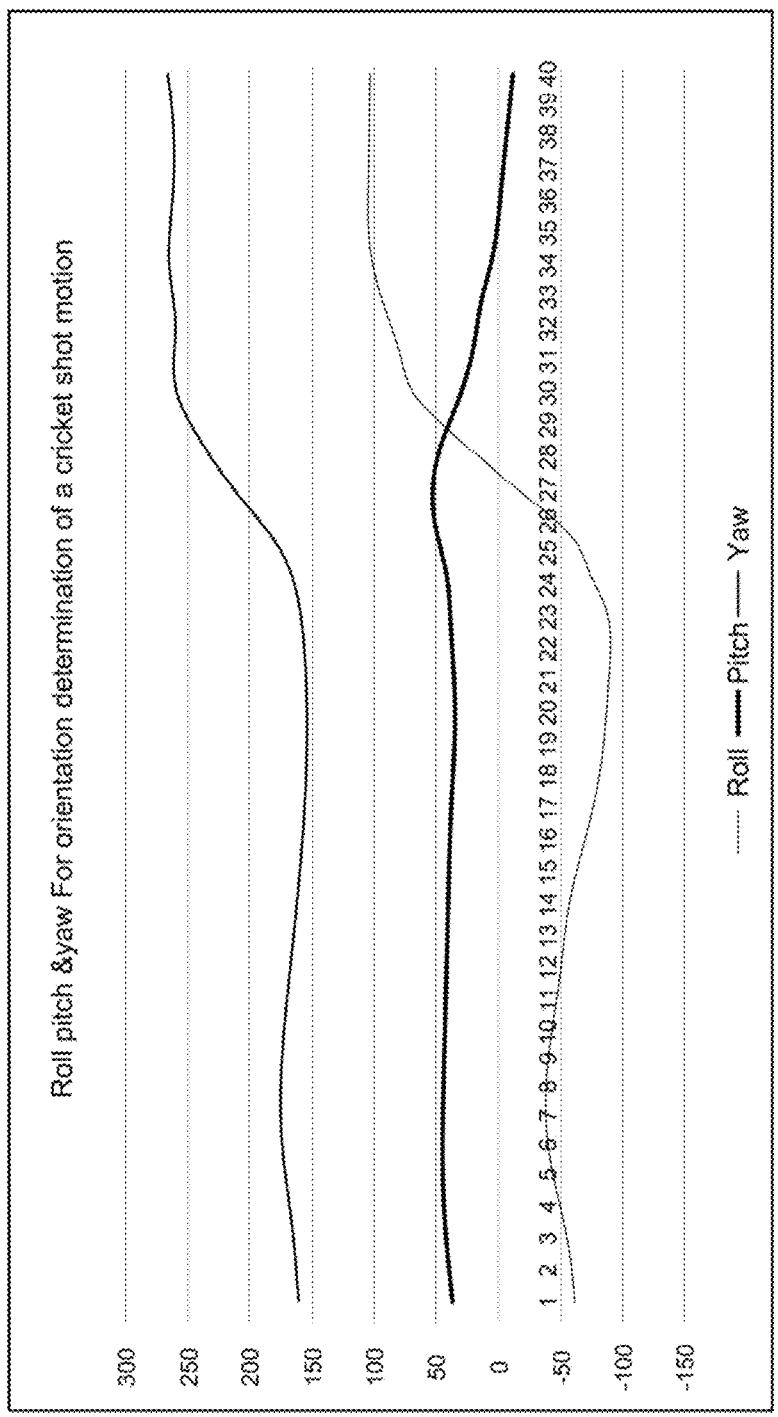
FIG. 17 illustrates a chart indicating an exemplary representation of an analysis of roll-pitch-yaw for determining an orientation of a cricket shot motion using a system for monitoring and analyzing the performance of a player, according to one embodiment herein.

FIG. 17 illustrates a chart indicating an exemplary representation of an analysis of roll-pitch-yaw for determining an orientation of a cricket shot motion using a system for monitoring and analyzing the performance of a player, according to one embodiment herein. The roll-pitch-yaw data are used to derive an angular motion of the bat. The quaternions and Roll, Pitch and Yaw is further used to understand the angular motion of the bat and is used by the gaming engine to show the angular movement of the bat.

Figure 18:
FIG. 18 illustrates an exemplary screenshot of a rendering of a scorecard analysis for a sportsperson such as a batsman in the game of cricket using a system for monitoring and analyzing the performance of a player, according to one embodiment herein.

FIG. 18 illustrates an exemplary screenshot of a rendering of a scorecard analysis for a sportsperson such as a batsman in the game of cricket using a system for monitoring and analyzing the performance of a player, according to one embodiment herein. The scorecard comprises details about the type of shot played by the sportsperson, the swing speed of the bat, the impact speed at the time of impact between the bat and ball, the angle of lift of the bat and a balance index of the overall shot played by the sportsperson.

Figure 19:
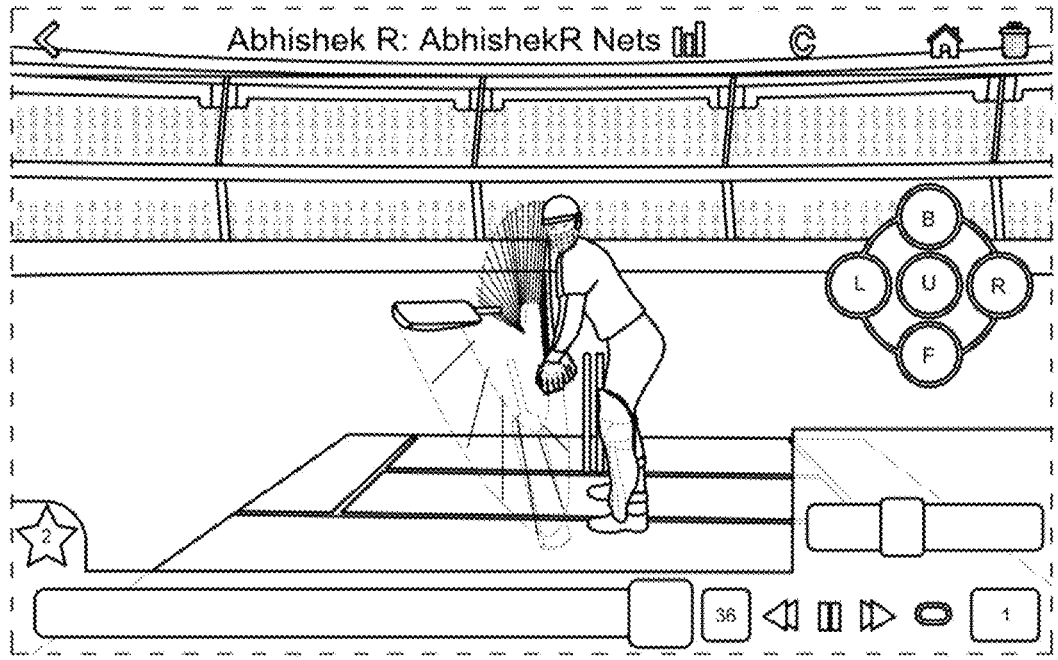
FIG. 19 illustrates an exemplary screenshot indicating a front view of a visual rendering of a sportsperson such as a batsman in the game of cricket using a system for monitoring and analyzing the performance of a player, according to one embodiment herein.

FIG. 19 illustrates an exemplary screenshot indicating a front view of a visual rendering of a sportsperson such as a batsman in the game of cricket using a system for monitoring and analyzing the performance of a player, according to one embodiment herein.

Figure 20:
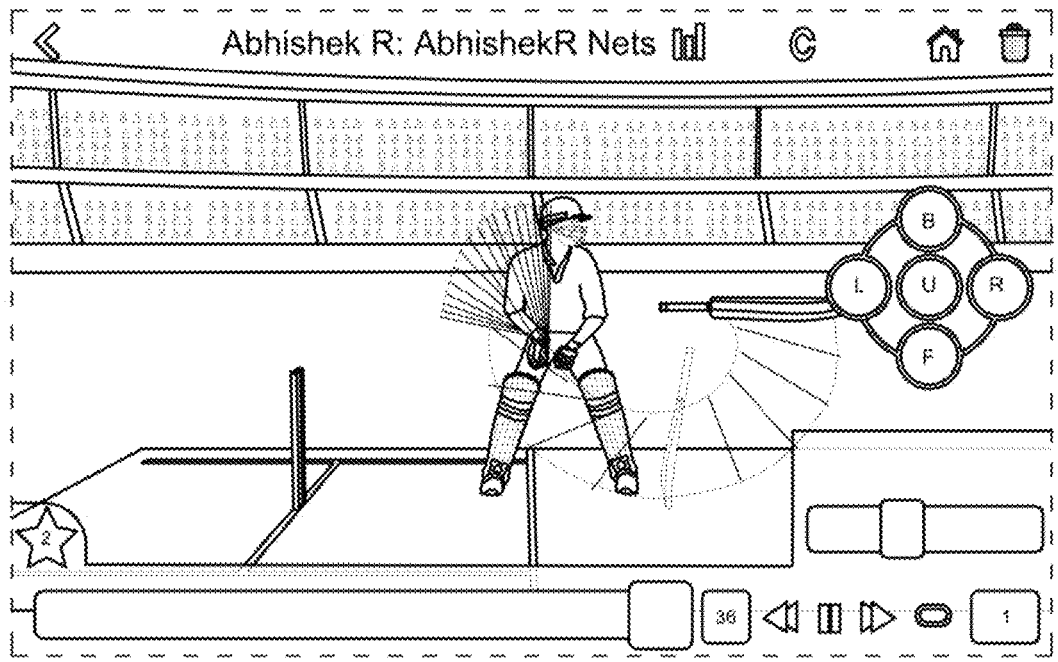
FIG. 20 illustrates an exemplary screenshot exhibiting a right-side view of a visual rendering of a sportsperson such as a batsman in the game of cricket using a system for monitoring and analyzing the performance of a player, according to one embodiment herein.

FIG. 20 illustrates an exemplary screenshot exhibiting a right-side view of a visual rendering of a sportsperson such as a batsman in the game of cricket using a system for monitoring and analyzing the performance of a player, according to one embodiment herein.

Figure 21:
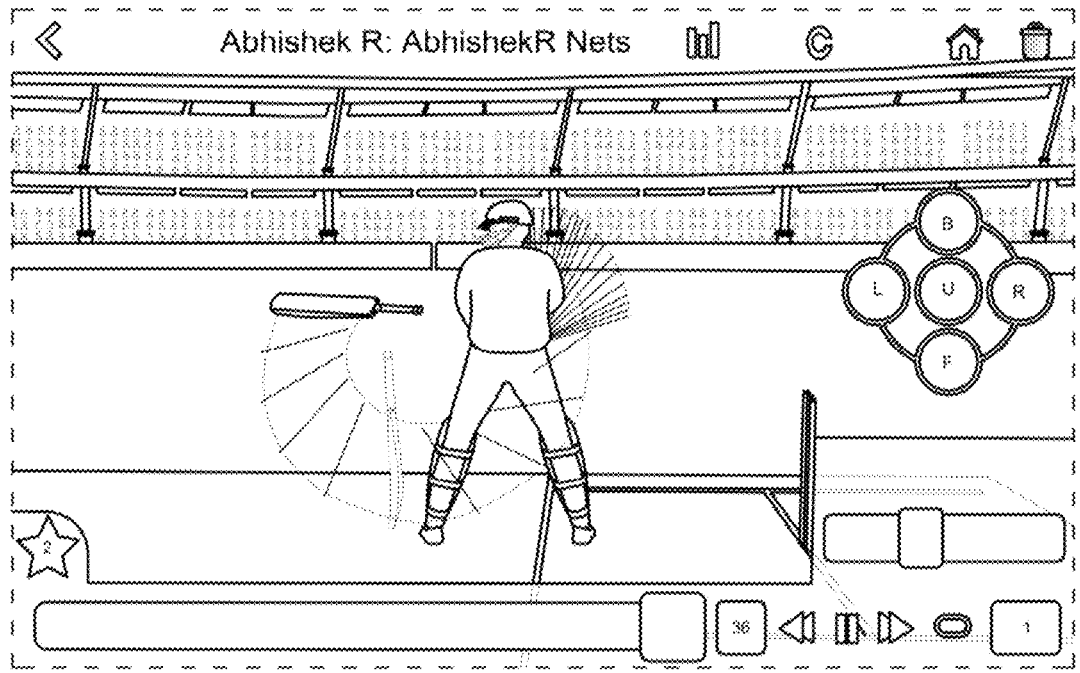
FIG. 21 illustrates an exemplary screenshot exhibiting a left-side view of a visual rendering of a sportsperson such as a batsman in the game of cricket using a system for monitoring and analyzing the performance of a player, according to one embodiment herein.

FIG. 21 illustrates an exemplary screenshot exhibiting a left-side view of a visual rendering of a sportsperson such as a batsman in the game of cricket using a system for monitoring and analyzing the performance of a player, according to one embodiment herein.

Figure 22:
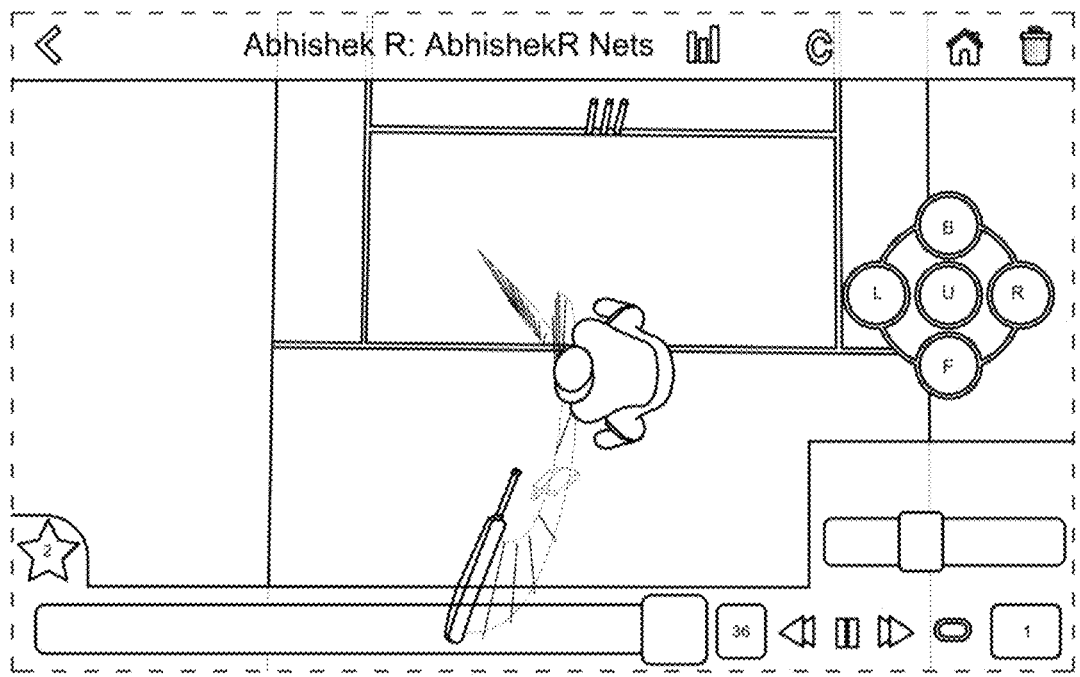
FIG. 22 illustrates an exemplary screenshot exhibiting a top side view of a visual rendering of a sportsperson such as a batsman in the game of cricket using a system for monitoring and analyzing the performance of a player, according to one embodiment herein.

FIG. 22 illustrates an exemplary screenshot exhibiting a top side view of a visual rendering of a sportsperson such as a batsman in the game of cricket using a system for monitoring and analyzing the performance of a player, according to one embodiment herein.

Figure 23A:
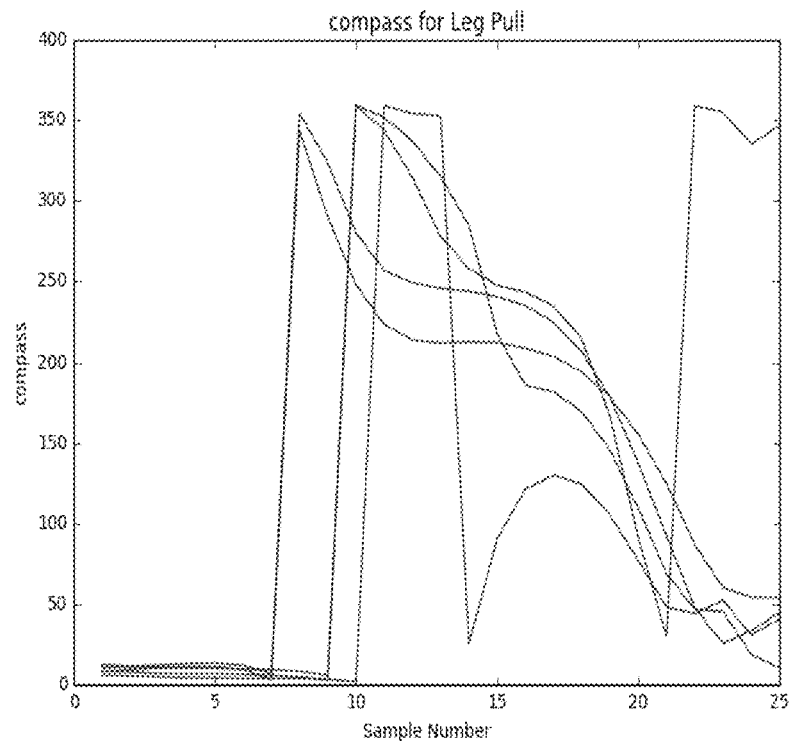
FIG. 23A illustrates a chart indicating an exemplary representation of an analysis of compass data for determining a leg pull using a system for monitoring and analyzing the performance of a player, according to one embodiment herein.

FIG. 23A illustrates a chart indicating an exemplary representation of an analysis of compass data for determining a leg pull using a system for monitoring and analyzing the performance of a player, according to one embodiment herein.

Figure 23B:
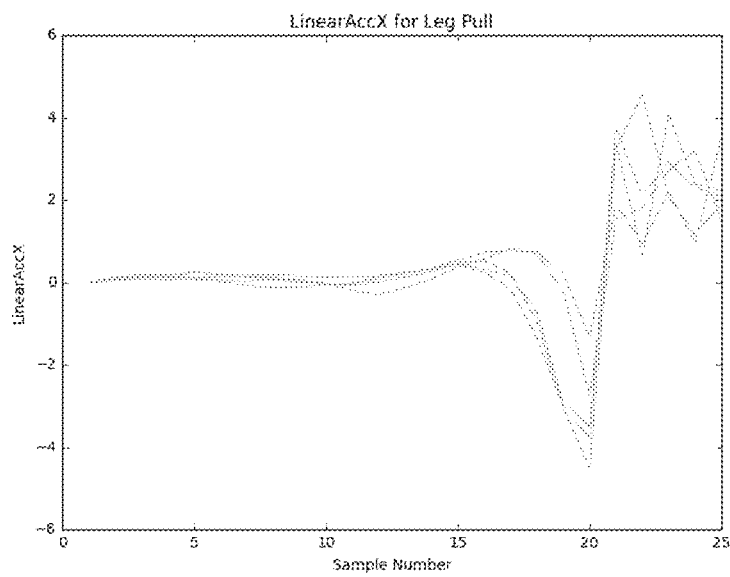
FIG. 23B illustrates a chart indicating an exemplary representation of an analysis of linear acceleration data on one axis for determining a leg pull using a system for monitoring and analyzing the performance of a player, according lo one embodiment herein.

FIG. 23B illustrates a chart indicating an exemplary representation of an analysis of linear acceleration data on one axis for determining a leg pull using a system for monitoring and analyzing the performance of a player, according to one embodiment herein.

Figure 23C:
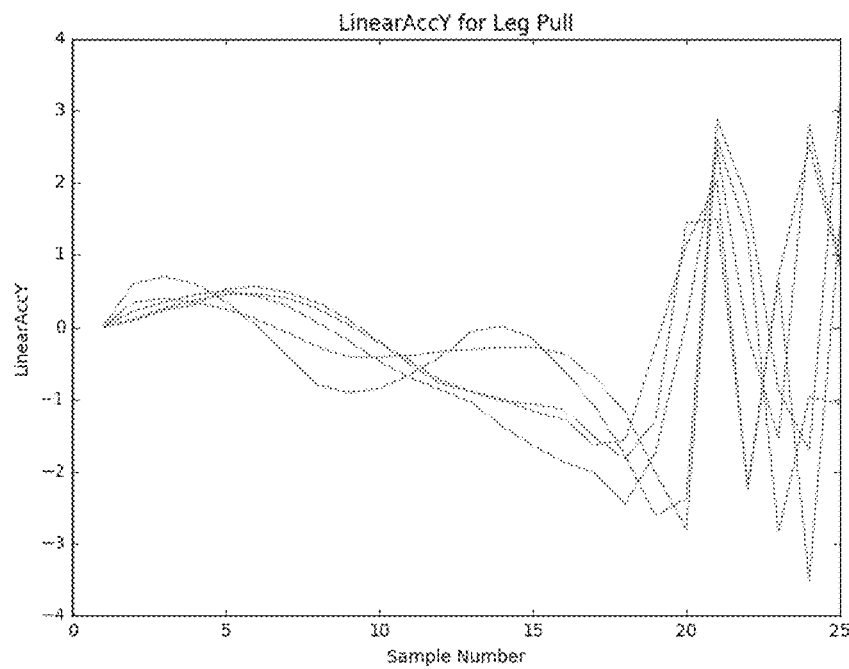
FIG. 23C illustrates a chart indicating an exemplary representation of an analysis of linear acceleration data on second axis for determining a leg pull using a system for monitoring and analyzing the performance of a player, seconding to one embodiment herein.

FIG. 23C illustrates a chart indicating an exemplary representation of an analysis of linear acceleration data on second axis for determining a leg pull using a system for monitoring and analyzing the performance of a player, according to one embodiment herein.

Figure 23D:
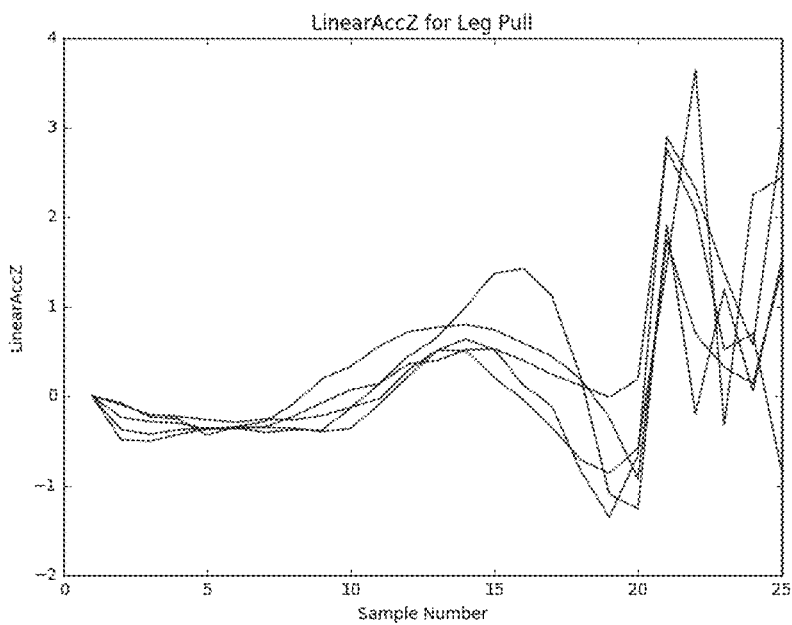
FIG. 23D illustrates a chart indicating an exemplary representation of an analysis of linear acceleration data on third axis for determining a leg pull using a system for monitoring and analyzing the performance of a player, according to one embodiment herein.

FIG. 23D illustrates a chart indicating an exemplary representation of an analysis of linear acceleration data on third axis for determining a leg pull using a system for monitoring and analyzing the performance of a player, according to one embodiment herein.

Figure 23E:
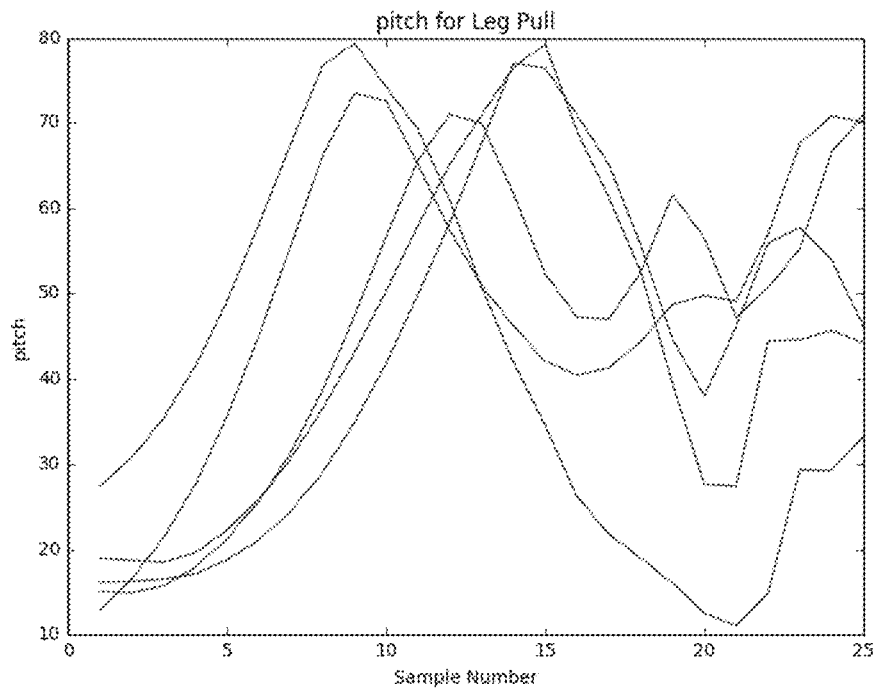
FIG. 23E illustrates a chart indicating an exemplary representation of an analysis of pitch data for determining a leg pull using a system for monitoring and analyzing the performance of a player, according to one embodiment herein.

FIG. 23E illustrates a chart indicating an exemplary representation of an analysis of pitch data for determining a leg pull using a system for monitoring and analyzing the performance of a player, according to one embodiment herein.

Figure 23F:
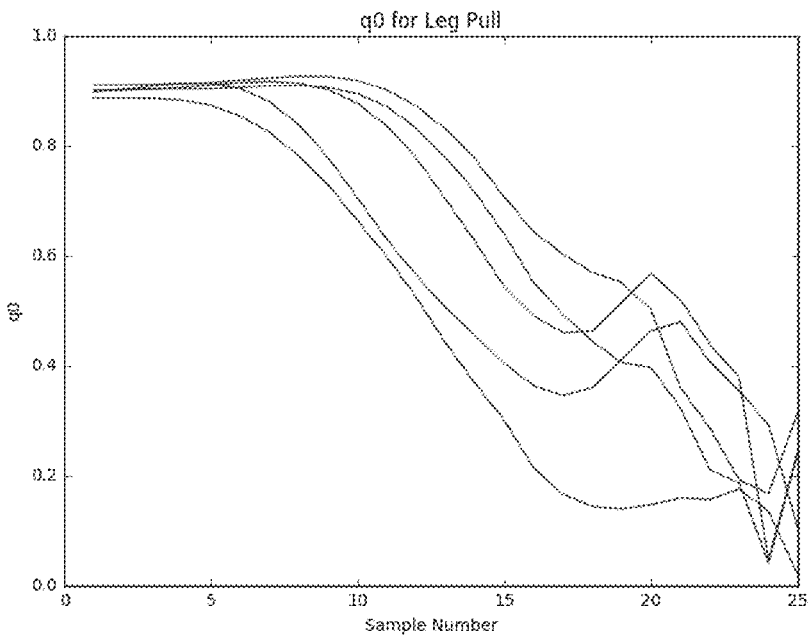
FIG. 23F illustrates a chart indicating an exemplary representation of an analysis of quaternions data (q0) for determining a leg pull using a system for monitoring and analyzing the performance of a player, according to one embodiment herein.

FIG. 23F illustrates a chart indicating an exemplary representation of an analysis of quadrinion data (q0) for determining a leg pull using a system for monitoring and analyzing the performance of a player, according to one embodiment herein.

Figure 23G:
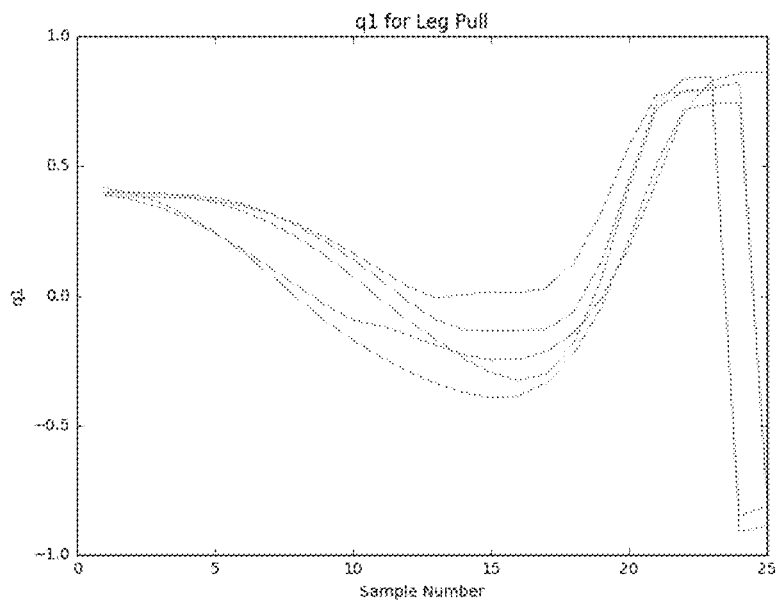
FIG. 23G illustrates a chart indicating an exemplary representation of an analysis of quaternions (q1) data for determining a leg pull using a system for monitoring and analyzing the performance of a player, according to one embodiment herein.

FIG. 23G illustrates a chart indicating an exemplary representation of an analysis of quadrillion (q1) data for determining a leg pull using a system for monitoring and analyzing the performance of a player, according to one embodiment herein.

Figure 23H:
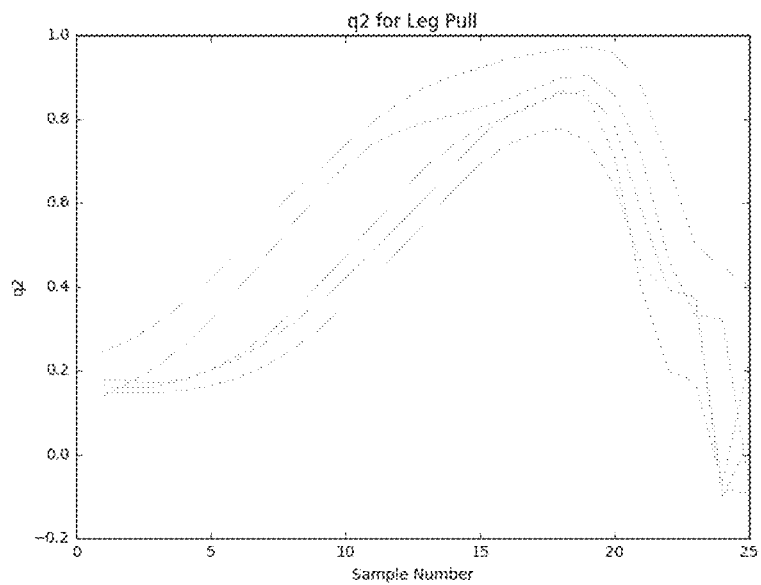
FIG. 23H illustrates a chart indicating an exemplary representation of an analysis of quaternions (q2) data for determining a leg pull using a system for monitoring and analyzing the performance of a player, according to one embodiment herein.

FIG. 23H illustrates a chart indicating an exemplary representation of an analysis of quadrinion (q2) data for determining a leg pull using a system for monitoring and analyzing the performance of a player, according to one embodiment herein.

Figure 23I:
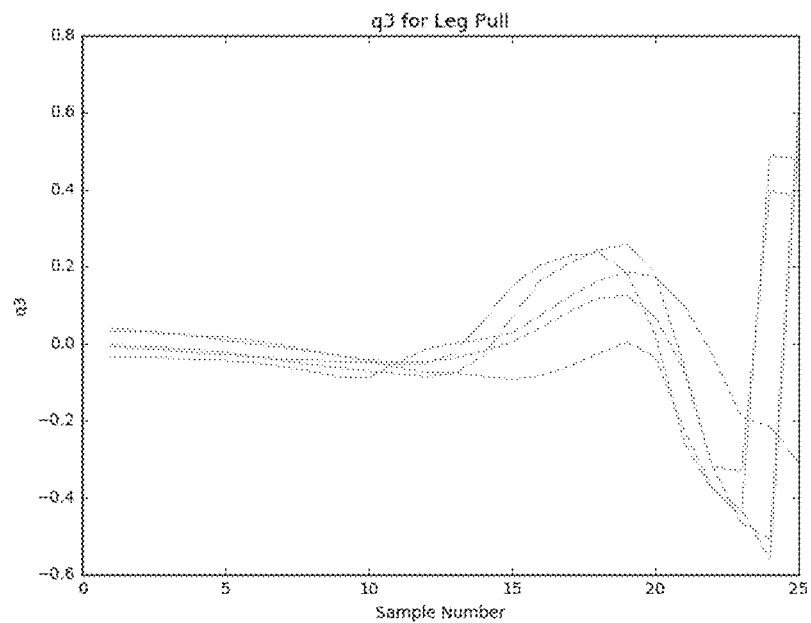
FIG. 23I illustrates a chart indicating an exemplary representation of an analysis of quaternions (q3) data for determining a leg pull using a system for monitoring and analyzing the performance of a player, according to one embodiment herein.

FIG. 23I illustrates a chart indicating an exemplary representation of an analysis of quadrinion (q3) data for determining a leg pull using a system for monitoring and analyzing the performance of a player, according to one embodiment herein.

Figure 23J:
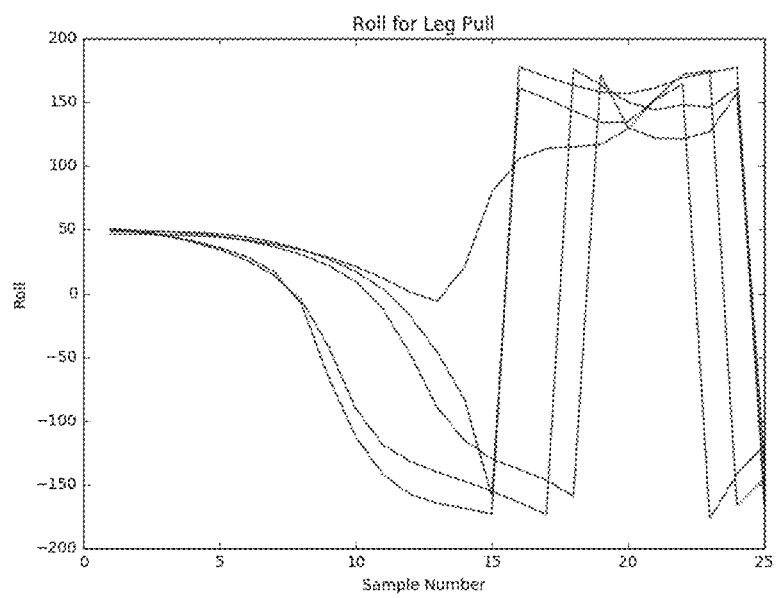
FIG. 23J illustrates a chart indicating an exemplary representation of an analysis of roll data for determining a leg pull using a system for monitoring and analyzing the performance of a player, according to one embodiment herein.

FIG. 23J illustrates a chart indicating an exemplary representation of an analysis of roll data for determining a leg pull using a system for monitoring and analyzing the performance of a player, according to one embodiment herein.

Figure 24A:
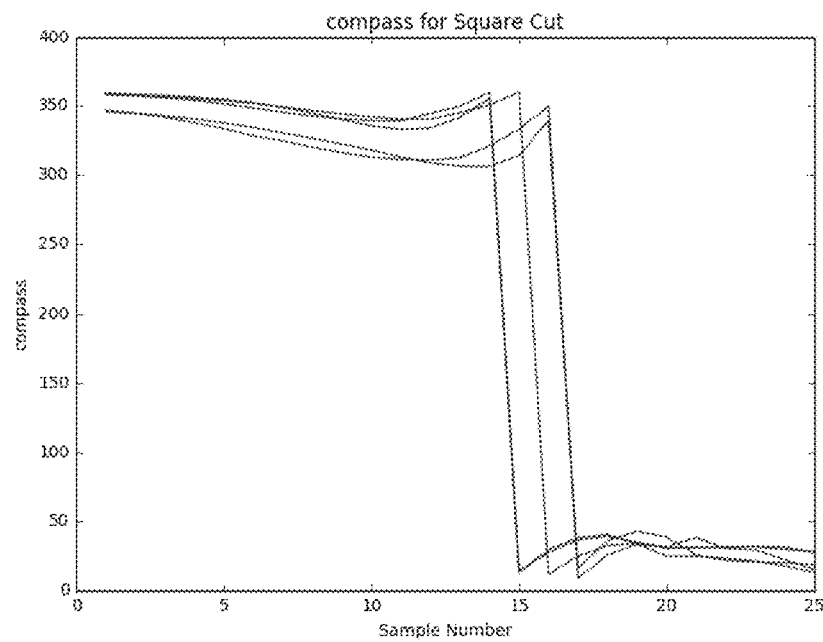
FIG. 24A illustrates a chart indicating an exemplary representation of an analysis of compass data for determining a square cut shot using a system for monitoring and analyzing the performance of a player, according to one embodiment herein.

FIG. 24A illustrates a chart indicating an exemplary representation of an analysis of compass data for determining a square cut shot using a system for monitoring and analyzing the performance of a player, according to one embodiment herein.

Figure 24B:
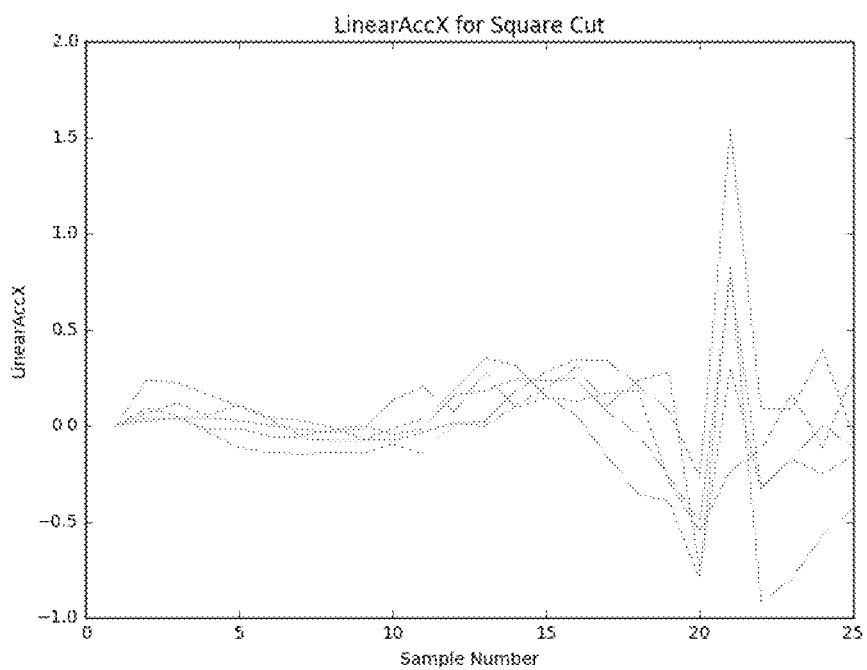
FIG. 24B illustrates a chart indicating an exemplary representation of an analysts of linear acceleration data on one axis for determining a square cut shot using a system for monitoring and analyzing the performance of a player, according to one embodiment herein.

FIG. 24B illustrates a chart indicating an exemplary representation of an analysis of linear acceleration data on one axis for determining a square cut shot using a system for monitoring and analyzing the performance of a player, according to one embodiment herein.

Figure 24C:
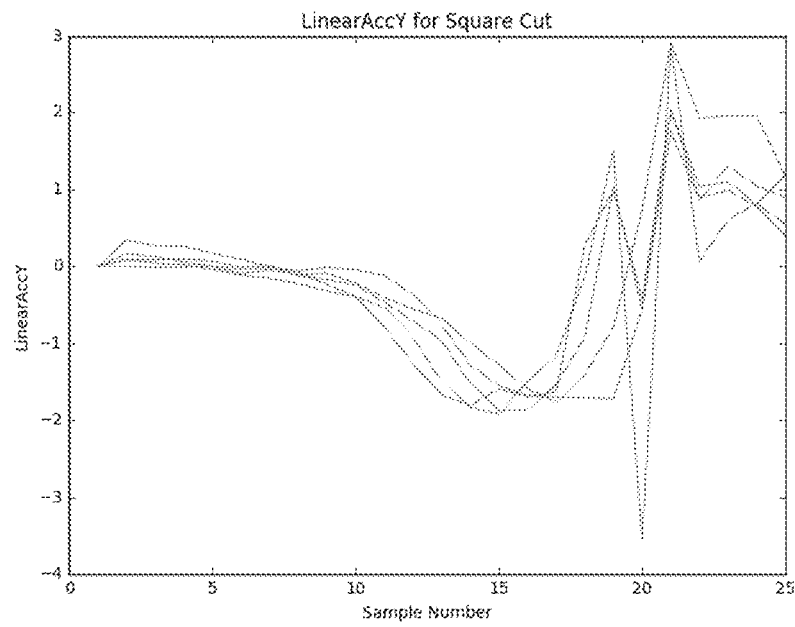
FIG. 24C illustrates a chart indicating an exemplary representation of an analysis of linear acceleration data on second axis for determining a square cut shot using a system for monitoring and analyzing the performance of a player, according to one embodiment herein.

FIG. 24C illustrates a chart indicating an exemplary representation of an analysis of linear acceleration data on second axis for determining a square cut shot using a system for monitoring and analyzing the performance of a player, according to one embodiment herein.

Figure 24D:
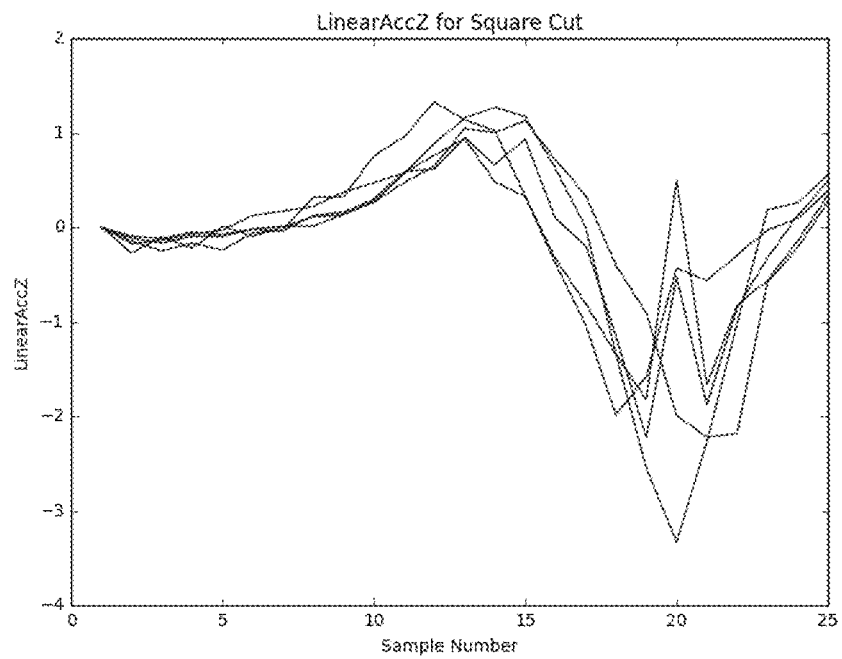
FIG. 24D illustrates a chart indicating an exemplary representation of an analysis of linear acceleration data on third axis for determining a square cut shot using a system for monitoring and analyzing the performance of a player, according to one embodiment herein.

FIG. 24D illustrates a chart indicating an exemplary representation of an analysis of linear acceleration data on third axis for determining a square cut shot using a system for monitoring and analyzing the performance of a player, according to one embodiment herein.

Figure 24E:
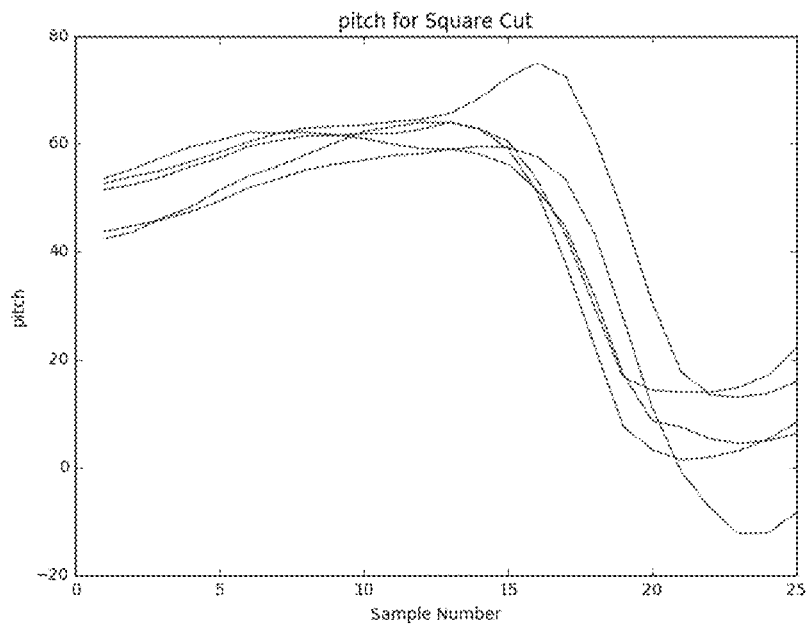
FIG. 24E illustrates a chart indicating an exemplary representation of an analysis of pitch data for determining a square cut shot using a system for monitoring and analyzing the performance of a player, according to one embodiment herein.

FIG. 24E illustrates a chart indicating an exemplary representation of an analysis of pitch data for determining a square cut shot using a system for monitoring and analyzing the performance of a player, according to one embodiment herein.

Figure 24F:
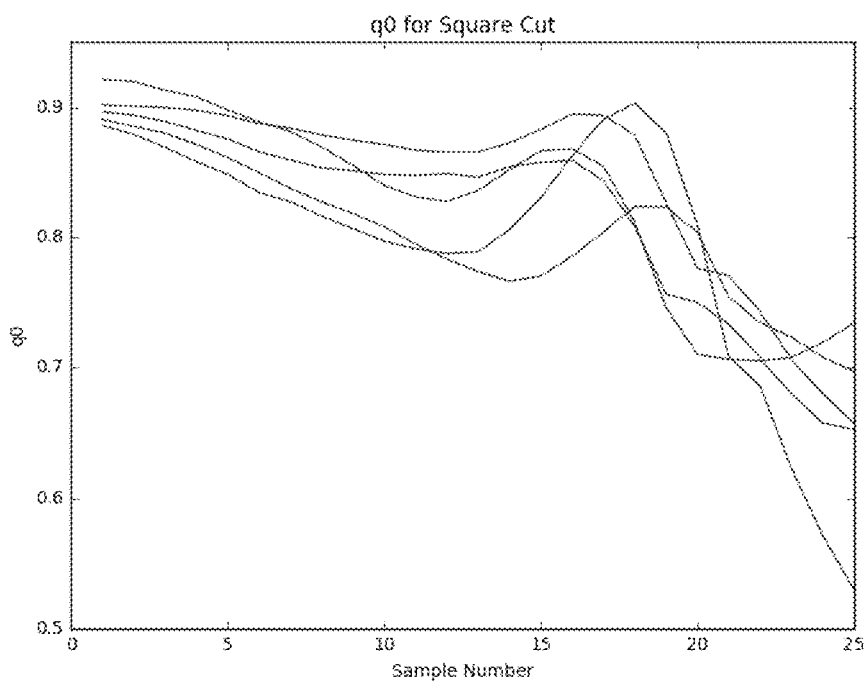
FIG. 24F illustrates a chart indicating an exemplary representation of an analysis of quaternions data (q0) for determining a square cut shot using a system for monitoring and analyzing the performance of a player, according to one embodiment herein.

FIG. 24F illustrates a chart indicating an exemplary representation of an analysis of quadrinion data (q0) for determining a square cut shot using a system for monitoring and analyzing the performance of a player, according to one embodiment herein.

Figure 24G:
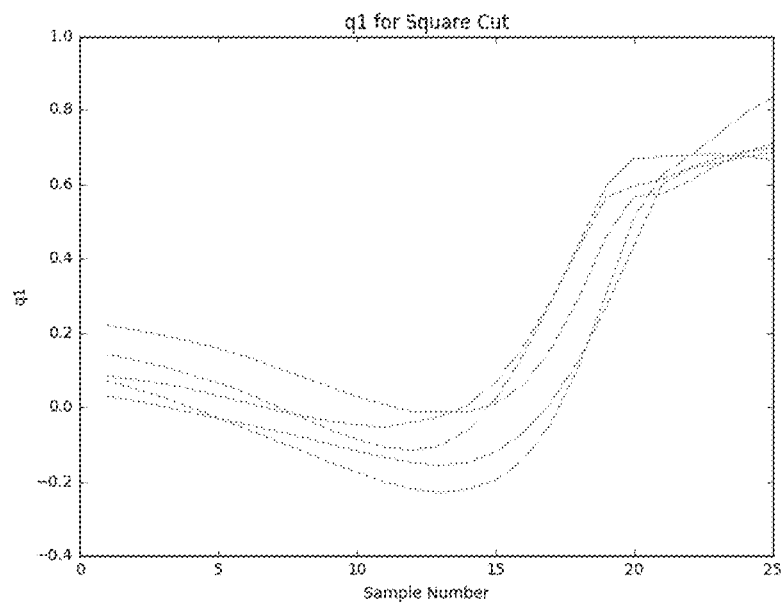
FIG. 24G illustrates a chart indicating an exemplary representation of an analysis of quaternions (q1) data for determining a square cut shot using a system for monitoring and analyzing the performance of a player, according to one embodiment herein.

FIG. 24G illustrates a chart indicating an exemplary representation of an analysis of quadrinion (q1) data for determining a square cut shot using a system for monitoring and analyzing the performance of a player, according to one embodiment herein.

Figure 24H:
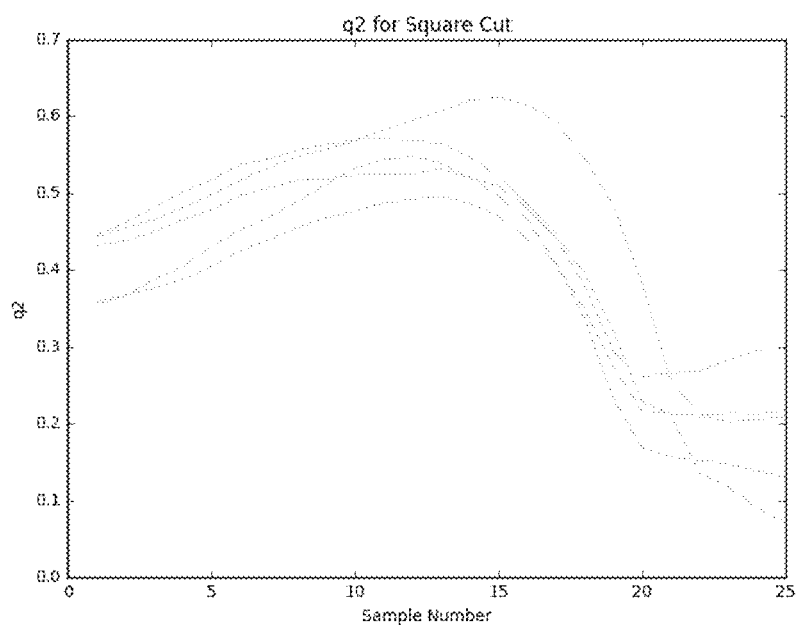
FIG. 24H illustrates a chart indicating an exemplary representation of an analysis of quaternions (q2) data for determining a square cut shot using a system for monitoring and analyzing the performance of a player, according to one embodiment herein.

FIG. 24H illustrates a chart indicating an exemplary representation of an analysis of quadrinion (q2) data for determining a square cut shot using a system for monitoring and analyzing the performance of a player, according to one embodiment herein.

Figure 24I:
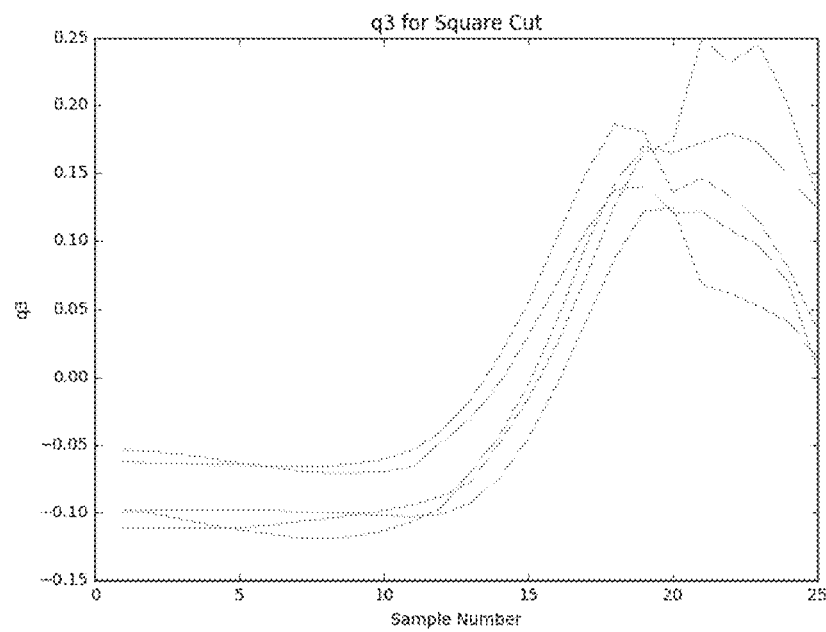
FIG. 24I illustrates a chart indicating an exemplary representation of an analysis of quaternions (q3) data for determining a square cut shot using a system for monitoring and analyzing the performance of a player, according to one embodiment herein.

FIG. 24I illustrates a chart indicating an exemplary representation of an analysis of quadrillion (q3) data for determining a square cut shot using a system for monitoring and analyzing the performance of a player, according to one embodiment herein.

Figure 24J:
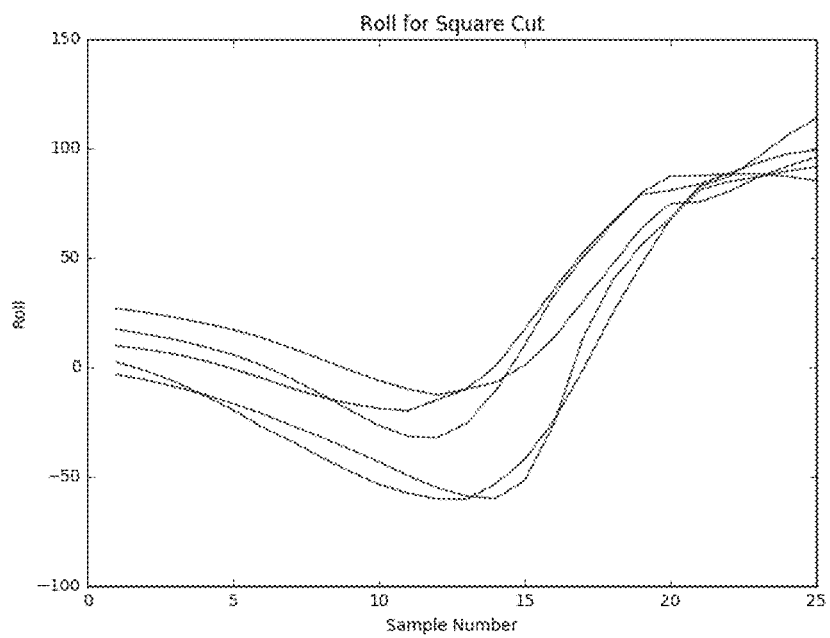
FIG. 24J illustrates a chart indicating aa exemplary representation of an analysis of roll data for determining a square cut shot using a system for monitoring and analyzing the performance of a player, according to one embodiment herein.

FIG. 24J illustrates a chart indicating an exemplary representation of an analysis of roll data for determining a square cut shot using a system for monitoring and analyzing the performance of a player, according to one embodiment herein.

Figure 25A:
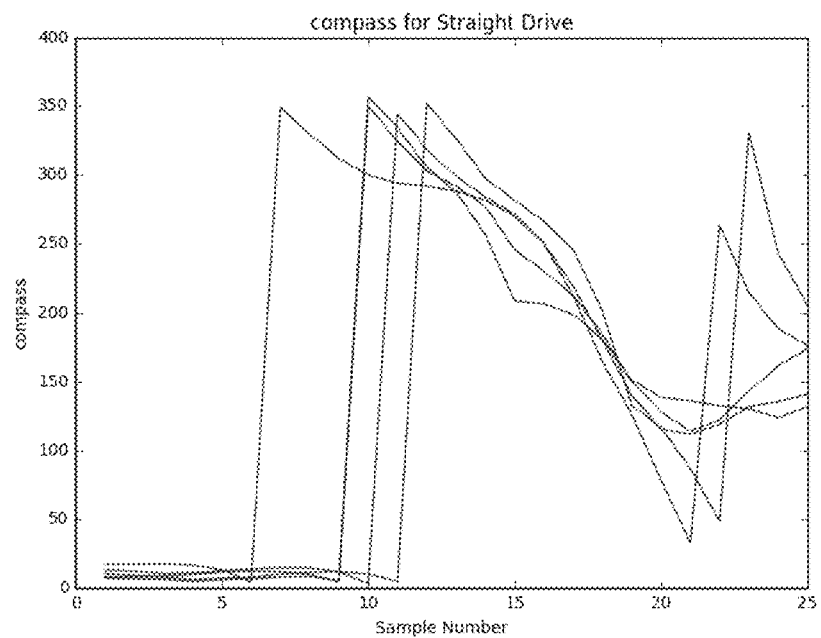
FIG. 25A illustrates a chart indicating an exemplary representation of an analysis of compass data for determining a straight drive shot using a system for monitoring and analyzing the performance of a player, according to one embodiment herein.

FIG. 25A illustrates a chart indicating an exemplary representation of an analysis of compass data for determining a straight drive shot using a system for monitoring and analyzing the performance of a player, according to one embodiment herein.

Figure 25B:
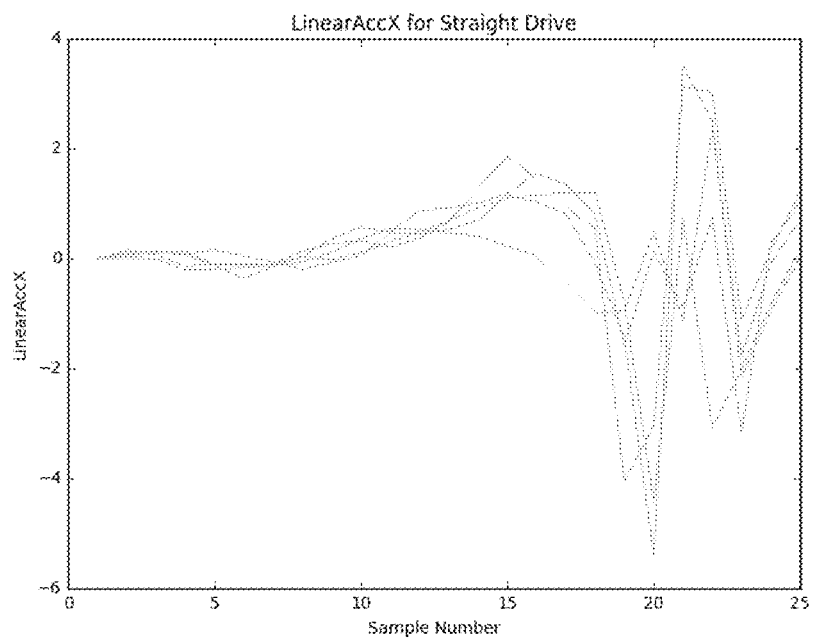
FIG. 25B illustrates a chart indicating an exemplary representation of an analysis of linear acceleration data on one axis for determining a straight drive shot using a system for monitoring and analyzing the performance of a player, according to one embodiment herein.

FIG. 25B illustrates a chart indicating an exemplary representation of an analysis of linear acceleration data on one axis for determining a straight drive shot using a system for monitoring and analyzing the performance of a player, according to one embodiment herein.

Figure 25C:
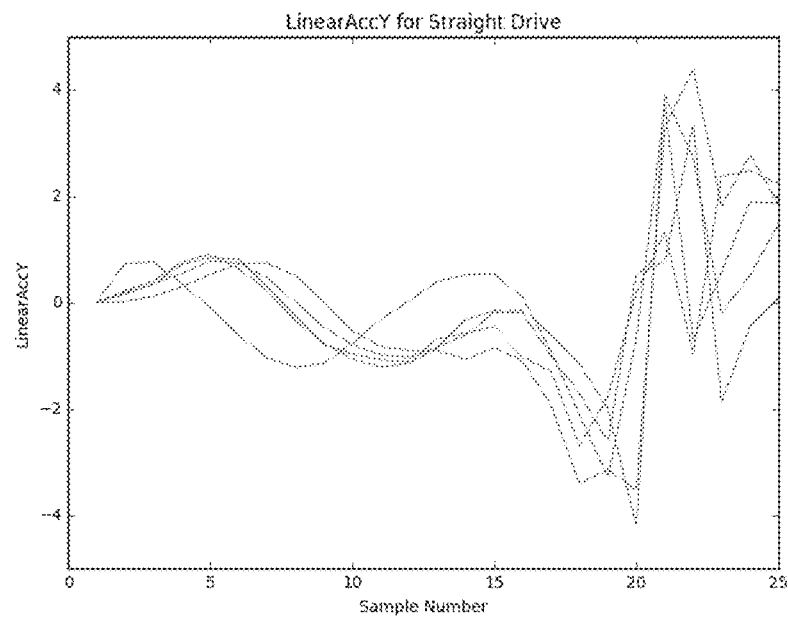
FIG. 25C illustrates a chart indicating an exemplary representation of an analysis of linear acceleration data on second axis for determining a straight drive shot using a system for monitoring and analyzing the performance of a player, according to one embodiment herein.

FIG. 25C illustrates a chart indicating an exemplary representation of an analysis of linear acceleration data on second axis for determining a straight drive shot using a system for monitoring and analyzing the performance of a player, according to one embodiment herein.

Figure 25D:
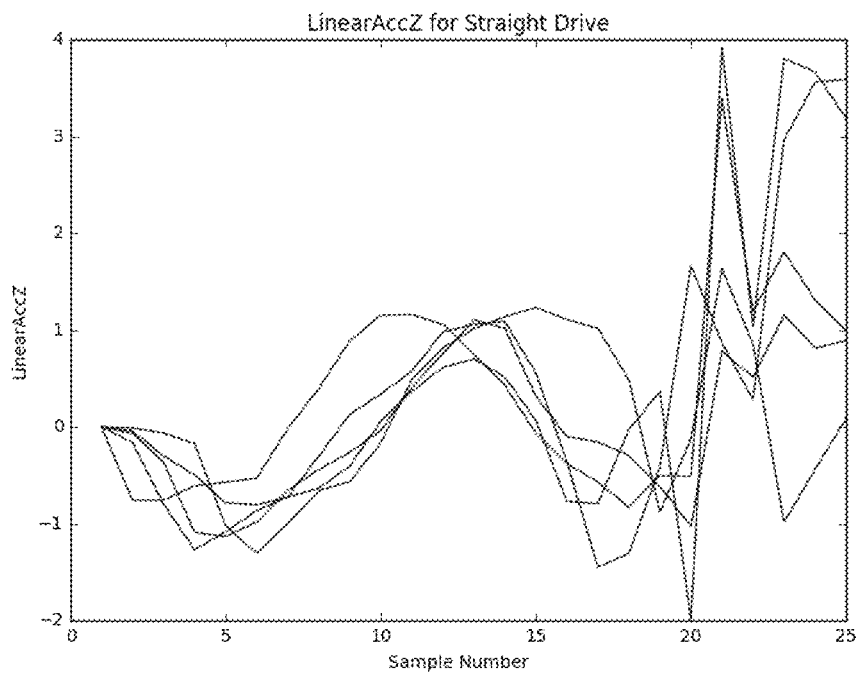
FIG. 25D illustrates a chart indicating an exemplary representation of an analysis of linear acceleration data on third axis for determining a straight drive shot using a system for monitoring and analyzing the performance of a player, according to one embodiment herein.

FIG. 25D illustrates a chart indicating an exemplary representation of an analysis of linear acceleration data on third axis for determining a straight drive shot using a system for monitoring and analyzing the performance of a player, according to one embodiment herein.

Figure 25E:
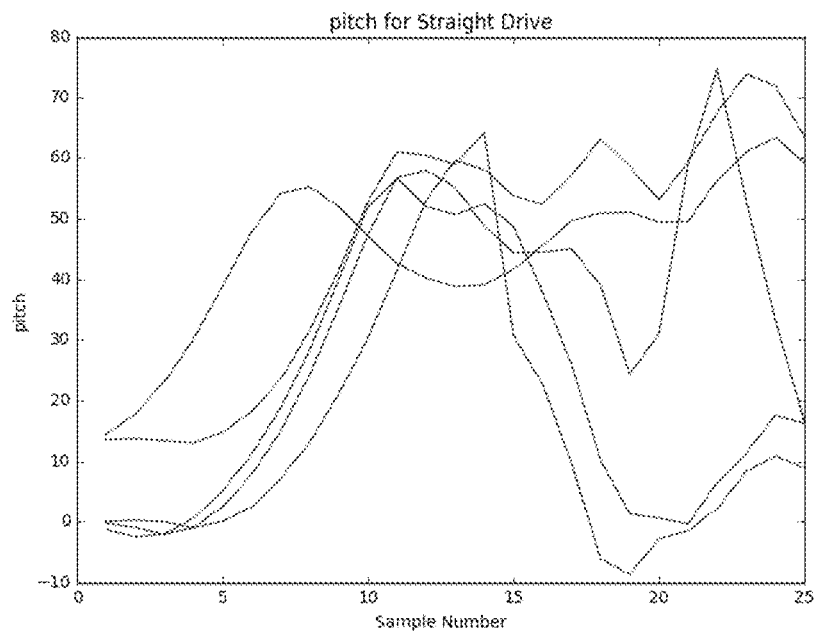
FIG. 25E illustrates a chart indicating an exemplary representation of an analysis of pitch data for determining a straight drive shot using a system for monitoring and analyzing the performance of a player, according to one embodiment herein.

FIG. 25E illustrates a chart indicating an exemplary representation of an analysis of pitch data for determining a straight drive shot using a system for monitoring and analyzing the performance of a player, according to one embodiment herein.

Figure 25F:
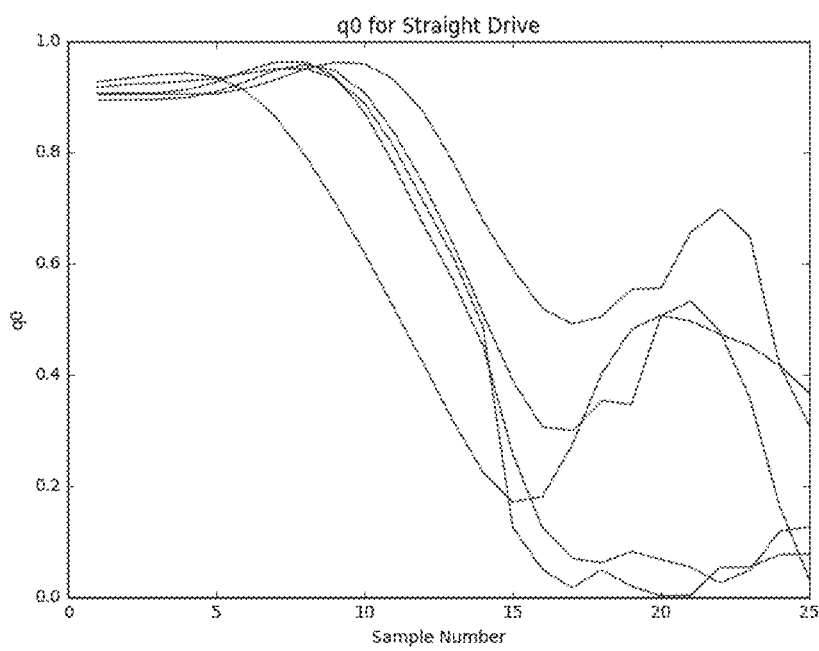
FIG. 25F illustrates a chart indicating an exemplary representation of an analysis of quaternions data (q0) for determining a straight drive shot using a system for monitoring and analyzing the performance of a player, according to one embodiment herein.

FIG. 25F illustrates a chart indicating an exemplary representation of an analysis of quadrillion data (q0) for determining a straight drive shot using a system for monitoring and analyzing the performance of a player, according to one embodiment herein.

Figure 25G:
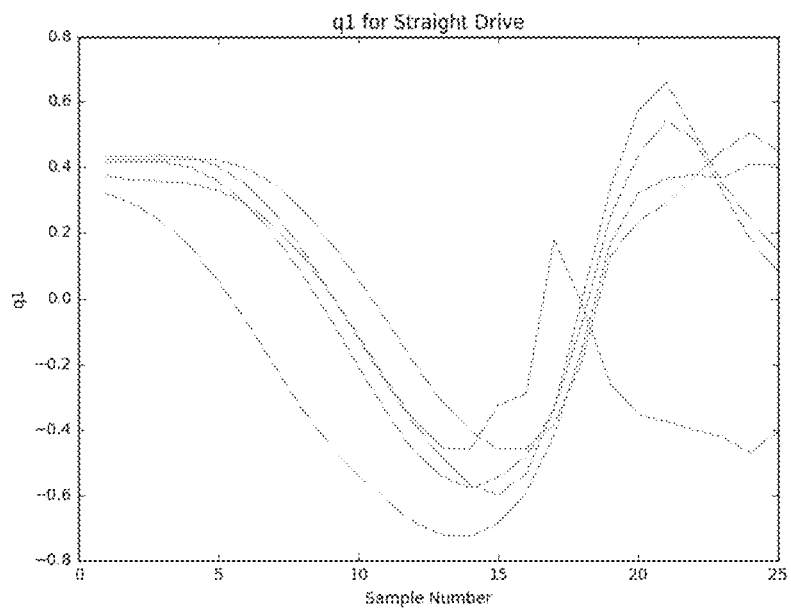
FIG. 25G illustrates a chart indicating an exemplary representation of an analysis of quaternions (q1) data for determining a straight drive shot using a system for monitoring and analyzing the performance of a player, according to one embodiment herein.

FIG. 25G illustrates a chart indicating an exemplary representation of an analysis of quadrillion (q1) data for determining a straight drive shot using a system for monitoring and analyzing the performance of a player, according to one embodiment herein.

Figure 25H:
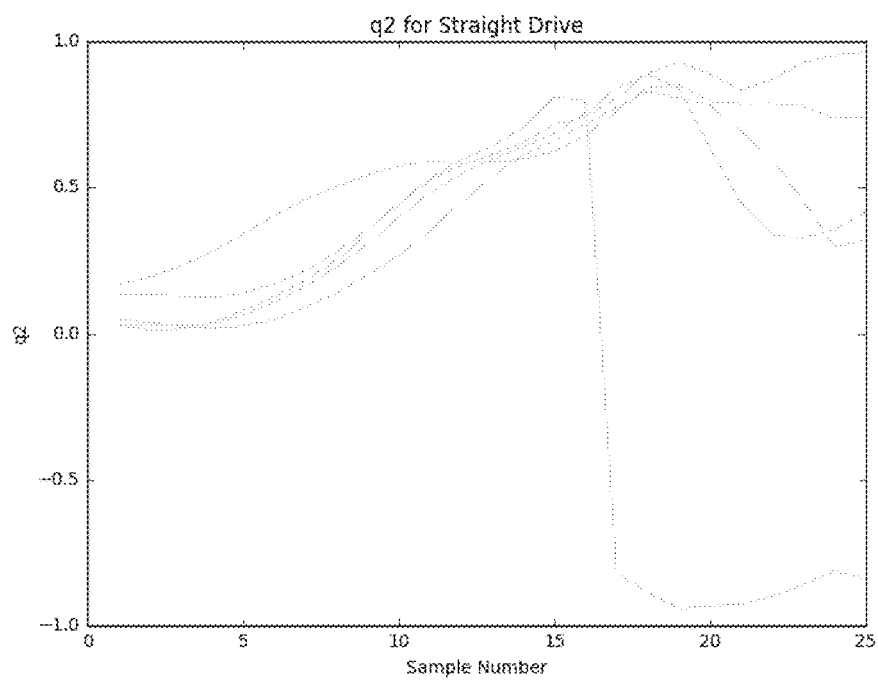
FIG. 25H illustrates a chart indicating an exemplary representation of an analysis of quaternions (q2) data for determining a straight drive shot using a system for monitoring and analyzing the performance of a player, according to one embodiment herein.

FIG. 25H illustrates a chart indicating an exemplary representation of an analysis of quadrinion (q2) data for determining a straight drive shot using a system for monitoring and analyzing the performance of a player, according to one embodiment herein.

Figure 25I:
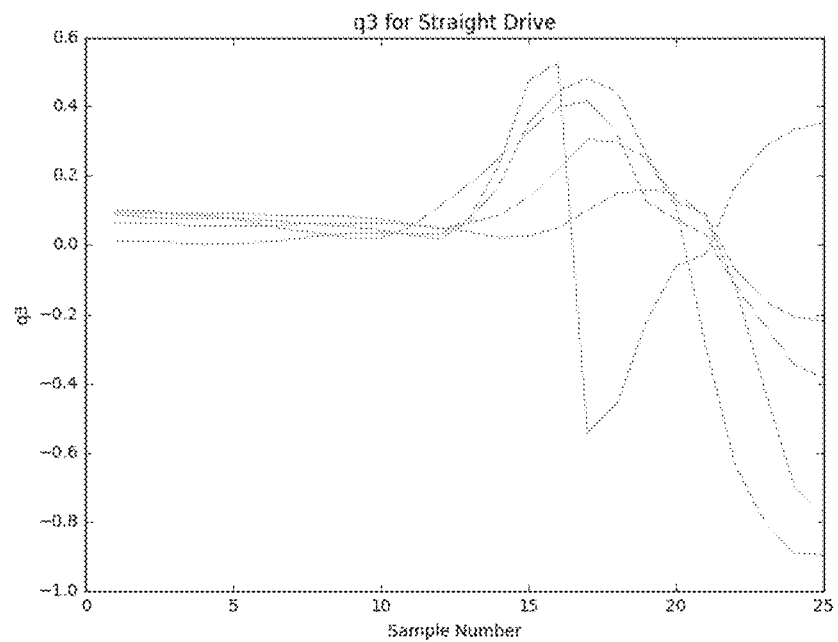
FIG. 25I illustrates a chart indicating an exemplary representation of an analysis of quaternions (q3) data for determining a straight drive shot using a system for monitoring and analyzing the performance of a player, according to one embodiment herein.

FIG. 25I illustrates a chart indicating an exemplary representation of an analysis of quadrinion (q3) data for determining a straight drive shot using a system for monitoring and analyzing the performance of a player, according to one embodiment herein.

Figure 25J:
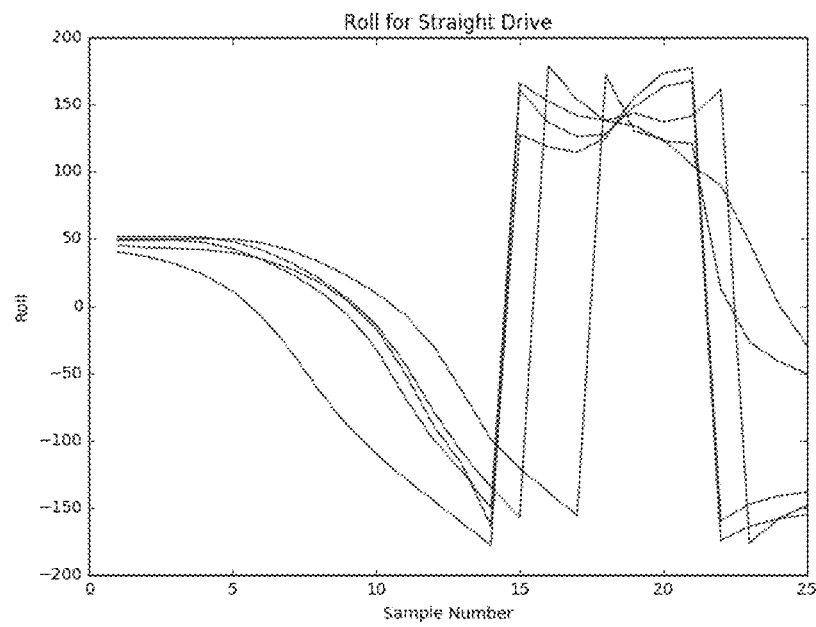
FIG. 25J illustrates a chart indicating an exemplary representation of an analysis of roll data for determining a straight drive shot using a system for monitoring and analyzing the performance of a player, according to one embodiment herein.

FIG. 25J illustrates a chart indicating an exemplary representation of an analysis of roll data for determining a straight drive shot using a system for monitoring and analyzing the performance of a player, according to one embodiment herein.

The various embodiments herein provide a system and method for monitoring and analyzing sports performance of an individual. The system helps the players to enhance the level of player's competence by improving skill levels. Further, the system and method processes the data collected with a plurality of sensors such as inertial motion units (IMU), to capture the motions of the bat, head position, and feet relative to the bat movement, to visually represent the movements in the form of an animation. This visual representation is done without using any video recording equipment. The system and method also provides a dashboard to enable the player to receive the feedback from a plurality of stakeholders such as coaches, mentors, sports scientists, clubs, teams, umpires, family and friends, and the like. Further, the system and method provides recommendations to the users on the possible improvements and the possible ways to eliminate and minimize mistakes. The system also brings the advantages of the video recording solutions used by the international and first class players to every player to help them to advance their game of play or game level at a fraction of the cost with much-reduced effort setup without actually using the video recording. The system enables to store the shot data for entire duration of the game on the game monitoring device itself without a requirement of any external connectivity. Further, the system and method enables to automatically recognize the various types of shots (straight drive, cover drive, square cut, etc.) of a batsman. Further, a comparative analysis of the shot played by the player with the corresponding best-in-class shot or best-in-class ball bowled. Additionally, the system also shares the data regarding the area the batsmen has intended to hit the shot, whether the shot was hit in the air or on the ground, whether the head was balanced, the time of hitting a shot by the batsman, the batting speed of batsman, and many such cricketing parameters which are important to monitor for one's improvement.

The foregoing description of the specific embodiments will so fully reveal the general nature of the embodiments herein that others can, by applying current knowledge, readily modify and/or adapt for various applications such specific embodiments without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. Therefore, while the embodiments herein have been described in term of preferred embodiments, those skilled in the art will recognize that the embodiments herein can be practiced with modification within the spirit and scope of the appended claims.

Although the embodiments herein are described with various specific embodiments, it will be obvious for a person skilled in the art to practice the disclosure with modifications. However, all such modifications are deemed to be within the scope of the appended claims.

It is also to be understood that the following claims are intended to cover all of the generic and specific features of the embodiments described herein and all the statements of the scope of the embodiments which as a matter of language might be said to fall there between.

What is claimed is:

1. A system for analysing sports and improving player performance by providing feedback in near real-time without any visual data capture mechanisms, the system comprising:
  a monitoring device, wherein the monitoring device comprises a microcontroller and a plurality of sensors, and the microcontroller analyses a plurality of data points or parameters collected by the plurality of sensors, and:
    the plurality of sensors are configured to detecting the plurality of data points or parameters from a plurality of actions and poses comprised in a physical motion of a player, and generate corresponding output signals, and the plurality of data points or parameters captured by the plurality of sensors includes a motion of the player, a speed at which the player hits a ball, a linear motion, an angular motion, a direction of a shot, an amount of pressure put on the ball by a bat, quaternions, linear acceleration in three axes, angular velocity, a plurality of rotational parameters including roll, pitch and yaw values, and a plurality of physiological features of the player, wherein:
    the plurality of sensors are communicatively connected through a communication network to synchronize capturing of at least one of the data points, the parameters, an event, and the physical motion;
    the plurality of sensors are configured to capture information corresponding to the event simultaneously and recreate the event from synchronously captured event information even when one of the plurality of sensors has failed to capture the event;
    one of the plurality of sensors located on the bat is configured to detect the impact of the ball on the bat to trigger and activate remaining sensors to start a recording operation of the actions of the player, using time of impact of the ball as a reference point for starting the recording operation of an action(s) of the player;
  wherein the microcontroller is configured to synchronize the plurality of sensors to generate a synchronized data output from the plurality of data points or parameters captured by the plurality of sensors;
  a remote server communicably coupled to a plurality of endpoint computing devices, wherein the remote server comprises a database, said remote server is configured to receive the synchronized output data and generate a visual simulation of the player and the actions of the player, without using any video recording equipment, and provide a simulation of the physical motion captured through the plurality of sensors in the plurality of endpoint computing devices;
  and said database is configured to:
    store an analysis data, a retrieval data, a metadata, and an information related to the physical motion of a plurality of players;
  and the remote server is configured to:
    analyse the output signals received from the plurality of sensors based on a preset rule(s) and a predetermined technique(s) to compare an action and a performance of the player with a reference template of practices of performing a physical motion, or the action, and a pose to provide a feedback to the player; and process the analysis data, the retrieval data, the metadata, and the information related to the physical motion of the plurality of players, stored in the database, and provide a predictive analytics on any one of the physical motion, the action, and the pose of the player at a plurality of levels;
    perform post-noise filtering and error correction in motion data received from at least some of said plurality of sensors and recreate the motion in a three-dimensional (3D) visual space using the plurality of data points or parameters measured by some of said plurality of sensors;
    derive a linear motion using a linear acceleration in three axes, and derive an angular motion using the quaternions and the plurality of rotational parameters;
  and a microphone is provided on a bat used by the player, and the microphone is connected to the monitoring device and configured to transmit audio information related to an impact of the bat with other player accessories to identify an accurate impact of the bat with the ball and assist in triangulating an exact impact time during a swing of the bat, and wherein the microphone module is configured to distinguish an actual action played with the bat and an unwanted action of the bat and the player.

2. The system according to claim 1, wherein the monitoring device comprises a gyroscope, an accelerometer, a magnetometer, a compass, a motion sensor(s), a temperature sensor(s), a pressure sensor(s), a position sensor(s), a proximity sensor(s), a speed sensor(s), an audio sensor, a pyroelectric sensor, a piezoelectric sensor, a memory, and a battery power supply.

3. The system according to claim 1, wherein the monitoring device comprises a communication circuit for transmitting the data points or parameters detected by the plurality of sensors to the remote server and the plurality of endpoint computing devices, and wherein the plurality of sensors are placed in a vicinity of the player or embedded in any of attires and sports equipment used by the player in performing the plurality of actions and poses, and wherein the microcontroller is configured to filter noise signals from the synchronized output data detect the data points or parameters, and process the output signals to derive a pattern.

4. The system according to claim 1, wherein the monitoring device is placed in a plurality of locations on a sports gear and an attire of the player, and the number of monitoring devices and the configuration of the monitoring devices is determined by a plurality of parameters, wherein the plurality of parameters includes location and placement of the monitoring device on the sports equipment, an impact threshold, a visual context, wherein the location and the placement of the monitoring device on the sports equipment is determined based on an axis orientation to be identified, three-axis of the device to be mapped, and a speed and range of motion of the sports equipment to be estimated, wherein a point of impact is captured using the impact threshold based on a type of sport and a type of sport activity, and wherein the parameters for determination of impact include acceleration and a rate of change of acceleration, and wherein the parameters for the visual context are configured specifically with respect to the type of sport activity, and wherein the sport activity is one of cricket, hockey, baseball, tennis, and table tennis.

5. The system according to claim 1, wherein the remote server is configured to analyse the synchronized output data from the monitoring device, and wherein the remote server is configured to contextually render the synchronized output data from the monitoring device in the plurality of endpoint computing devices based on preset rules, wherein the plurality of endpoint devices are configured to to access the analysis data, the retrieval data, the metadata, and the information related to the physical motion stored in the database, and wherein the plurality of endpoint devices are further configured to analyse stored past data of the actions and poses and the motion of the player, and quantitatively analyse the actions by comparing preset or observed data for said player or a plurality of other players.

6. The system according to claim 1, wherein the remote server is configured to analyse the synchronized output data from the monitoring device based on preset parameters, wherein the preset parameters include a position of the bat, the direction of the shot, a type of the shot, a swing analysis, a shot analysis, a direction analysis, a pressure analysis, an audio analysis, a pattern determination, a comparative analysis, a virtual replay of the game, and mechanics of the game.

7. The system according to claim 1, wherein the remote server is configured to provide a comparison of an action of the player with a reference action, wherein the remote server is configured to provide a guidance on necessary changes and improvements needed to reach to a level of the reference action.

8. The system according to claim 1, wherein the remote server is configured to combine an analysis of each shot to derive an analysis report for each delivery, shot, game, session, and player, and the remote server is configured to combine a plurality of game patterns of the player to derive optimum factors for the player, and the optimum factors for the player includes a body dynamics of the player relative to a position of the bat at the time of impact.

9. The system according to claim 1, wherein the remote server is configured to automatically identify a type of the shot, wherein said remote server is further configured to generate an automated audio and text commentary of the physical motion and the action and poses captured.

10. The system according to claim 1, wherein the remote server is configured to learn from a stored historical data of the player so as to provide the predictive analytics at a plurality of levels, wherein the plurality of levels include nda player level analytics, a game level analytics, and a match level analytics, and the remote server is configured to predict common mistakes or errors made by the player based on an analysis of previous games and to provide a recommendation to help the player to overcome the common mistakes or errors in a game on action, and wherein the remote server is configured to provide recommendations to enhance skill and performance of the player.

11. The system according to claim 1, wherein the system further comprises a user interface for displaying analysis, visuals, and results computed by the remote server wherein the user interface is configured to display information related to the player and the game, and information displayed on the user interface includes a visual playback of previous shots played by the player, analysis and visualization of the previous shots played by the player, analysis and visualization of previous games played by the player, comparative analysis of the game and shots of the player with a plurality of other players.

12. The system according to claim 1, wherein the monitoring device comprises an impact sensor, wherein the impact sensor is configured to detect and determine an impact of the ball on the bat, and the impact sensor is configured to determine a position of the plurality of sensors attached to the bat, the ball and the player.

13. The system according to claim 5, wherein the remote server is configured to identify patterns from the observed data and provide contextual suggestions on the plurality of endpoint computing devices.

14. A method for analyzing sports and improving player performance by providing feedback in near real-time without any visual data capture mechanisms, the method comprising:

collecting a plurality of data points with a plurality of sensors provided in a monitoring device;

configuring a microcontroller of the monitoring device to detect the plurality of data points from a plurality of actions and poses comprised in a physical motion of a player, and wherein the plurality of data points a motion of the player, a speed at which the player hits a ball, a linear motion, an angular motion, a direction of the shot, an amount of pressure put on the ball by a bat, quaternions, linear acceleration in three axes, angular velocity, a plurality of rotational parameters including roll, pitch and yaw values, and a plurality of physiological features of the player;

transmitting audio information related to an impact of the bat with other player accessories by a microphone provided on the bat used by the player, and identifying an accurate impact of the bat with the ball and triangulating an exact impact time during a swing of the bat, wherein the microphone connected to the monitoring device and configured to distinguish an actual action played with the bat and an unwanted action of the bat and the player;

pairing a plurality of endpoint computing devices with the monitoring device for processing collected data points and a plurality of corresponding output signals;

synchronizing, using the microcontroller, the data points collected from the plurality of sensors to generate synchronized output data and recreating or simulating an action of the player in near real-time, wherein one of the plurality of sensors acts as a point of reference for synchronizing the data points from the plurality of sensors;

processing the synchronized output data at the plurality of endpoint computing devices or a remote server to provide a visual feedback on the actions and poses of the player;

generating and rendering a visual simulation of the actions and poses captured by the plurality of sensors on the plurality of endpoint computing devices, without a need of any video recording equipment; and contextually rendering processed output data in the plurality of endpoint computing devices; and wherein the method further includes configuring the remote server to:

analyse the output signals received from the plurality of sensors based on preset rules and predetermined techniques and compare an action and a performance of the player with a reference template of best practices or ways of performing the physical motion, or an action, or a pose to provide a feedback to the player for the improving the performance of the player;

trigger the database to store analysis data, retrieval data, metadata, and information related to physical motion of a plurality of players;

process the analysis data, the retrieval data, the metadata, and the information related to the physical motions of the plurality of players to provide a predictive analytics on any one of the physical motion, action, and the pose of the player at a plurality of levels;

perform post-noise filtering and error correction in motion data received from at least some of said plurality of sensors, and recreate the motion in a three-dimensional (3D) visual space using the plurality of data points measured by the at least some of said plurality of sensors;

derive linear motion using the linear acceleration in three axes, and derive angular motion using the quaternions and the plurality of rotational parameters;

and wherein the method further includes:

communicatively coupling the plurality of sensors through a communication network and synchronizing capturing of at least one of the data points, an event, and the physical motion, and configuring the plurality of sensors to simultaneously capture information corresponding to the event;

configuring the plurality of sensors to recreate the event from synchronously captured information even when one of the plurality of sensors has failed to capture the event;

configuring one of the plurality of sensors on the bat to detect the impact of the ball on the bat and activate all the plurality of sensors to start a recording operation of the actions of the player, and wherein the time of impact is a reference point for starting the recording operation of the actions of the player.

15. The method according to claim 14, further comprising the steps of:

transmitting collected data points to the plurality of endpoint computing devices or the remote server through a communication circuit configured in the monitoring device;

detecting the data points and processing the output signals to derive a pattern; and synchronizing the plurality of data points received from the plurality of sensors to generate the visual simulation of the player and the actions of the player in near real time.

16. The method according to claim 14, wherein an analysis of the output data from the monitoring device is performed by the remote server, and wherein the output data is contextually rendered in the plurality of endpoint computing devices by the remote server based on preset rules, and wherein the plurality of endpoint computing devices are configured to access the analysis data, the retrieval data, the metadata, and the information related to the physical motion of the plurality of players, stored in the database.

17. The method according to claim 14, wherein the method includes analysing the synchronized output data from the monitoring device based on preset parameters, and wherein the preset parameters include a position of the bat, the direction of the shot, a type of the shot, a swing analysis, a shot analysis, a direction analysis, a pressure analysis, an audio analysis, a pattern determination, a comparative analysis, a virtual replay of a game, and a mechanics of the game.

18. The method according to claim 14, wherein the method further includes combining an analysis of each shot to derive an analysis report for each delivery, shot, game, session, and player, and combine a plurality of game patterns of the player to derive optimum factors for the player, and wherein the optimum factors for the player includes a body dynamics of the player relative to a position of the bat at the time of impact.

19. The method according to claim 14, wherein the method includes generating an automated audio and text commentary of the physical motion, the actions and the poses captured by the plurality of sensors.

20. The method according to claim 14, wherein the remote server is configured to learn from stored historical data of the player to provide the predictive analytics at a plurality of levels, and the plurality of levels include a player level analytics, a game level analytics, and a match level analytics, and the remote server is configured to predict common mistakes or errors made by the player based on an analysis of previous games to provide a recommendation to help the player to overcome the common mistakes or errors in a game on action, and wherein the remote server is configured to provide recommendations to enhance skill and performance of the player.

21. The method according to claim 14, wherein the method further includes configuring the plurality of endpoint computing devices to analyse the stored past data of the physical actions, poses and motion of the player and quantitatively analyse the physical actions, by comparing preset or observed data from same player or a plurality of other players.

22. The method according to claim 14, comprising displaying analysis, visuals and results computed by the remote server on a user interface, and configuring the user interface to display information of the player and a game on the plurality of endpoint computing devices, wherein the information displayed includes a visual playback of previous shots played by the player, an analysis and a visualization of the previous shots played by the player, an analysis and a visualization of previous games played by the player, and a comparative analysis of the game and shots of the player with a plurality of other players.

23. The method according to claim 14, wherein the monitoring device comprises an impact sensor, wherein the impact sensor is configured to detect and determine an impact of the ball on the bat, wherein the impact sensor is configured to determine a position of the plurality of sensors attached to the bat, the ball and the player.

24. The method according to claim 21, wherein the method further includes identifying patterns from the observed data and providing contextual suggestions.

\* \* \* \* \*